(12) United States Patent
Rojkova et al.

(10) Patent No.: US 12,059,270 B2
(45) Date of Patent: Aug. 13, 2024

(54) SYSTEMS AND METHODS FOR NOISE REMOVAL IN AN OPTICAL MEASUREMENT SYSTEM

(71) Applicant: HI LLC, Los Angeles, CA (US)

(72) Inventors: Viktoria Rojkova, Los Angeles, CA (US); Julian Kates-Harbeck, Marina Del Rey, CA (US)

(73) Assignee: HI LLC, Culver City, CA (US)

( * ) Notice: Subject to any disclaimer, the term of this patent is extended or adjusted under 35 U.S.C. 154(b) by 615 days.

(21) Appl. No.: 17/233,033

(22) Filed: Apr. 16, 2021

(65) Prior Publication Data

US 2021/0330266 A1 Oct. 28, 2021

Related U.S. Application Data

(60) Provisional application No. 63/138,159, filed on Jan. 15, 2021, provisional application No. 63/015,012, filed on Apr. 24, 2020.

(51) Int. Cl.
*A61B 5/00* (2006.01)
*G16H 40/67* (2018.01)

(52) U.S. Cl.
CPC .......... *A61B 5/7203* (2013.01); *A61B 5/0082* (2013.01); *A61B 5/6803* (2013.01);
(Continued)

(58) Field of Classification Search
CPC ... A61B 5/7203; A61B 5/0082; A61B 5/6803; A61B 5/7246; G16H 40/67
See application file for complete search history.

(56) References Cited

U.S. PATENT DOCUMENTS 4,018,534 A 4/1977 Thorn et al.
4,207,892 A 6/1980 Binder
(Continued)

FOREIGN PATENT DOCUMENTS

CN 200950235 9/2007
CN 107865635 4/2018
(Continued)

OTHER PUBLICATIONS

"emojipedia.org", https://emojipedia.org (accessed May 27, 2021).
(Continued)

*Primary Examiner* — Baisakhi Roy
(74) *Attorney, Agent, or Firm* — ALG Intellectual Property, LLC

(57) ABSTRACT

An illustrative optical measurement system includes a light source configured to emit light directed at a target within a user. The system further includes a detector configured to detect photon arrival times for photons of the light after the light is scattered by the target. The system further includes a processor configured to determine, based on the photon arrival times, histogram data associated with the target, the histogram data including noise. The processor is further configured to determine, based on the photon arrival times, a random matrix corresponding to the photon arrival times. The processor is further configured to determine, based on the random matrix, a noise distribution representing a distribution of the noise within the histogram data. The processor is further configured to generate clean histogram data using the noise distribution to filter at least a portion of the noise from the histogram data.

25 Claims, 20 Drawing Sheets

(52) U.S. Cl.
CPC .......... *A61B 5/7246* (2013.01); *G16H 40/67* (2018.01); *A61B 2562/0238* (2013.01)

(56) References Cited

U.S. PATENT DOCUMENTS

| | | |
|---|---|---|
| 4,281,645 A | 8/1981 | Jobsis |
| 4,321,930 A | 3/1982 | Jobsis |
| 4,515,165 A | 5/1985 | Carroll |
| 4,655,225 A | 4/1987 | Dahne et al. |
| 4,928,248 A | 5/1990 | Takahashi et al. |
| 4,963,727 A | 10/1990 | Cova |
| 4,995,044 A | 2/1991 | Blazo |
| 5,088,493 A | 2/1992 | Giannini |
| 5,090,415 A | 2/1992 | Yamashita |
| 5,309,458 A | 5/1994 | Carl |
| 5,386,827 A | 2/1995 | Chance et al. |
| 5,528,365 A | 6/1996 | Gonatas et al. |
| 5,625,458 A | 4/1997 | Alfano et al. |
| 5,761,230 A | 6/1998 | Oono et al. |
| 5,853,370 A | 12/1998 | Chance et al. |
| 5,895,984 A | 4/1999 | Renz |
| 5,929,982 A | 7/1999 | Anderson |
| 5,983,120 A | 11/1999 | Groner et al. |
| 5,987,045 A | 11/1999 | Albares et al. |
| 6,163,715 A | 12/2000 | Larsen et al. |
| 6,240,309 B1 | 5/2001 | Yamashita et al. |
| 6,384,663 B2 | 5/2002 | Cova et al. |
| 6,541,752 B2 | 4/2003 | Zappa et al. |
| 6,640,133 B2 | 10/2003 | Yamashita |
| 6,683,294 B1 | 1/2004 | Herbert et al. |
| 6,748,254 B2 | 6/2004 | O'Neil |
| 6,992,772 B2 | 1/2006 | Block |
| 7,095,491 B2 | 8/2006 | Forstner et al. |
| 7,356,365 B2 | 4/2008 | Schurman |
| 7,507,596 B2 | 3/2009 | Yaung et al. |
| 7,547,872 B2 | 6/2009 | Niclass et al. |
| 7,613,504 B2 | 11/2009 | Rowe |
| 7,667,400 B1 | 2/2010 | Goushcha |
| 7,705,284 B2 | 4/2010 | Inoue et al. |
| 7,714,292 B2 | 5/2010 | Agarwal et al. |
| 7,774,047 B2 | 8/2010 | Yamashita et al. |
| 7,899,506 B2 | 3/2011 | Xu et al. |
| 8,026,471 B2 | 9/2011 | Itzler |
| 8,078,250 B2 | 12/2011 | Chen et al. |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,352,012 B2 | 1/2013 | Besio |
| 8,633,431 B2 | 1/2014 | Kim |
| 8,637,875 B2 | 1/2014 | Finkelstein et al. |
| 8,754,378 B2 | 6/2014 | Prescher et al. |
| 8,817,257 B2 | 8/2014 | Herve |
| 8,937,509 B2 | 1/2015 | Xu et al. |
| 8,986,207 B2 | 3/2015 | Li |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,101,279 B2 | 8/2015 | Ritchey et al. |
| 9,131,861 B2 | 9/2015 | Ince et al. |
| 9,157,858 B2 | 10/2015 | Claps |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,282,932 B2 * | 3/2016 | Kudo ............... A61B 10/0041 |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,478,579 B2 | 10/2016 | Dai et al. |
| 9,529,079 B1 | 12/2016 | Droz |
| 9,535,157 B2 | 1/2017 | Caley et al. |
| 9,574,936 B2 | 2/2017 | Heinonen |
| 9,625,580 B2 | 4/2017 | Kotelnikov et al. |
| 9,627,569 B2 | 4/2017 | Harmon |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | Mcgarvey et al. |
| 9,671,284 B1 | 6/2017 | Dandin |
| 9,681,844 B2 | 6/2017 | Xu et al. |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,804,092 B2 | 10/2017 | Zeng et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,867,250 B1 | 1/2018 | Powers et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara' et al. |
| 9,939,316 B2 | 4/2018 | Scott et al. |
| 9,939,536 B2 | 4/2018 | O'Neill et al. |
| 9,946,344 B2 | 4/2018 | Ayaz et al. |
| D817,553 S | 5/2018 | Aaskov et al. |
| 9,983,670 B2 | 5/2018 | Coleman |
| 10,016,137 B1 | 7/2018 | Yang et al. |
| D825,112 S | 8/2018 | Saez |
| 10,056,415 B2 | 8/2018 | Na et al. |
| 10,103,513 B1 | 10/2018 | Zhang et al. |
| 10,141,458 B2 | 11/2018 | Zhang et al. |
| 10,157,954 B2 | 12/2018 | Na et al. |
| 10,158,038 B1 | 12/2018 | Do Valle et al. |
| 10,219,700 B1 | 3/2019 | Yang et al. |
| 10,256,264 B2 | 4/2019 | Na et al. |
| 10,340,408 B1 | 7/2019 | Katnani |
| 10,424,683 B1 | 9/2019 | Do Valle |
| 10,483,125 B2 | 11/2019 | Inoue |
| 10,515,993 B2 | 12/2019 | Field et al. |
| 10,533,893 B2 | 1/2020 | Leonardo |
| 10,558,171 B2 | 2/2020 | Kondo |
| 10,594,306 B2 | 3/2020 | Dandin |
| 10,627,460 B2 | 4/2020 | Alford et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,825,847 B2 | 11/2020 | Furukawa |
| 10,912,504 B2 | 2/2021 | Nakaji |
| 10,976,386 B2 | 4/2021 | Alford |
| 10,983,177 B2 | 4/2021 | Jiménez-Martínez |
| 10,996,293 B2 | 5/2021 | Mohseni |
| 11,006,876 B2 | 5/2021 | Johnson |
| 11,006,878 B2 | 5/2021 | Johnson |
| 2004/0057478 A1 | 3/2004 | Saito |
| 2004/0078216 A1 | 4/2004 | Toto |
| 2004/0160996 A1 | 8/2004 | Giorgi et al. |
| 2005/0061986 A1 | 3/2005 | Kardynal et al. |
| 2006/0197452 A1 | 9/2006 | Zhang |
| 2007/0038116 A1 | 2/2007 | Yamanaka |

(56) References Cited

U.S. PATENT DOCUMENTS

| | | |
|---|---|---|
| 2007/0083097 A1 | 4/2007 | Fujiwara |
| 2008/0021341 A1 | 1/2008 | Harris et al. |
| 2009/0012402 A1 | 1/2009 | Mintz |
| 2009/0163775 A1 | 6/2009 | Barrett |
| 2009/0313048 A1 | 12/2009 | Kahn et al. |
| 2010/0210952 A1 | 8/2010 | Taira et al. |
| 2011/0208675 A1 | 8/2011 | Shoureshi et al. |
| 2012/0029304 A1 | 2/2012 | Medina et al. |
| 2012/0101838 A1 | 4/2012 | Lingard et al. |
| 2013/0030267 A1 | 1/2013 | Lisogurski |
| 2013/0032713 A1 | 2/2013 | Barbi et al. |
| 2013/0144644 A1 | 6/2013 | Simpson |
| 2013/0221221 A1 | 8/2013 | Bouzid et al. |
| 2013/0342835 A1 | 12/2013 | Blacksberg |
| 2014/0027607 A1 | 1/2014 | Mordarski et al. |
| 2014/0066783 A1 | 3/2014 | Kiani |
| 2014/0185643 A1 | 7/2014 | Mccomb et al. |
| 2014/0191115 A1 | 7/2014 | Webster et al. |
| 2014/0211194 A1 | 7/2014 | Pacala et al. |
| 2014/0253713 A1* | 9/2014 | Zhai ............... G01N 21/17 348/80 |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1* | 6/2016 | Roukes ............... A61B 5/4029 600/476 |
| 2016/0161600 A1 | 6/2016 | Eldada et al. |
| 2016/0181302 A1 | 6/2016 | Mcgarvey et al. |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0341656 A1 | 11/2016 | Liu et al. |
| 2016/0343129 A1* | 11/2016 | Novikov ............ G01R 33/5608 |
| 2016/0345880 A1 | 12/2016 | Nakaji et al. |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0047372 A1 | 2/2017 | Mcgarvey et al. |
| 2017/0052065 A1 | 2/2017 | Sharma et al. |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2018/0003821 A1 | 1/2018 | Imai |
| 2018/0014741 A1 | 1/2018 | Chou |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0120404 A1* | 5/2018 | Novikov ............... G06T 7/0016 |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inoue et al. |
| 2019/0006399 A1 | 1/2019 | Otake et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0167211 A1 | 6/2019 | Everman et al. |
| 2019/0175068 A1 | 6/2019 | Everdell |
| 2019/0200888 A1 | 7/2019 | Poltorak |
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0088811 A1 | 3/2020 | Mohseni |
| 2020/0109481 A1 | 4/2020 | Sobek |
| 2020/0123416 A1 | 4/2020 | Bhattacharyya |
| 2020/0182692 A1 | 6/2020 | Lilic |
| 2020/0191883 A1 | 6/2020 | Bhattacharyya |
| 2020/0196932 A1 | 6/2020 | Johnson |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0076972 A1* | 3/2021 | Novikov ............ G01R 33/5608 |
| 2021/0013974 A1 | 5/2021 | Seidman |
| 2021/0139742 A1 | 5/2021 | Seidman |

FOREIGN PATENT DOCUMENTS

| | | |
|---|---|---|
| EP | 0656536 | 4/2004 |
| EP | 2294973 | 3/2011 |
| EP | 3419168 | 12/2018 |

(56) References Cited

FOREIGN PATENT DOCUMENTS

| | | |
|---|---|---|
| EP | 3487072 | 5/2019 |
| WO | 8804034 | 6/1988 |
| WO | 1999053577 | 10/1999 |
| WO | 2008144831 | 12/2008 |
| WO | 2012135068 | 10/2012 |
| WO | 2013034770 | 3/2013 |
| WO | 2013066959 | 5/2013 |
| WO | 2015052523 | 4/2015 |
| WO | 2015109005 | 7/2015 |
| WO | 2016166002 | 10/2016 |
| WO | 2017004663 | 1/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |

OTHER PUBLICATIONS

"International Search Report and Written Opinion received in International Application No. PCT/2021/018188".
"International Search Report and Written Opinion received in International Application No. PCT/US2021/018155".
"International Search Report and Written Opinion received in International Application No. PCT/US2021/018187".
"International Search Report and Written Opinion received in International Application No. PCT/US2021/018190".
"scienceofpeople.com/emojis", https://www.scienceofpeople.com/emojis/ (accessed May 27, 2021).
Hebert, et al., "Spatiotemporal image correlation spectroscopy (STICS) theory, verification, and application to protein velocity mapping in living CHO cells", Biophysical journal 88, No. 5 (2005): 3601-3614.
Kheng, et al., "Image Processing", https://www.comp.nus.edu.sg/~cs4243/lecture/imageproc.pdf, Mar. 9, 2014.
Sneha, et al.,"Understanding Correlation", https://www.allaboutcircuits.com/technical-articles/understanding- correlation/, Jan. 4, 2017.
Xu, et al., "A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.
Zucconi, et al., "The Autocorrelation Function", https://www.alanzucconi.com/2016/06/06/autocorrelation-function/, Jun. 6, 2016.
Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680.
Bellis, et al., "Photon counting imaging: the DigitalAPD", Society of Photo-Optical Instrumentation Engineers (SPIE) Conference Series, Feb. 2006, vol. 6068, pp. 111-120.
Blutman, et al., "A 0.1 pJ Freeze Vernier Time-to-Digital Converter in 65nm CMOS", 2014 International Symposium on Circuits and Systems (ISCAS), Melbourne, Australia.
Bruus, Henrik et al., Energy Level Statistics of the Two-Dimensional Hubbard Model at Low Filling, The American Physical Society. Physical Review B, vol. 55, No. 14, Apr. 1, 1997-II.
Cambie, et al., "Every photon counts: understanding and optimizing photon paths in luminescent solar concentrator-based photomicroreactors (LSC-PMs)", React. Chem. Eng., 2017, 2, 561-566.
Contini, et al., "Photon migration through a turbid slab described by a model based on diffusion approximation. I. Theory", Appl. Opt. 36(19), 4587 (1997).
Dalla Mora, et al., "Fast-Gated Single-Photon Avalanche Diode for Wide Dynamic Range Near Infrared Spectroscopy", IEEE Journal of Selected Topics in Quantum Electronics, vol. 16, No. 4, Jul./Aug. 2010.
Dalla Mora, et al., "Memory effect in silicon time-gated single-photon avalanche diodes", http://dx.doi.org/10.1063/1.4915332, Journal of Applied Physics 117, 114501, 2015.
De Heyn, et al., "A fast start-up 3GHz-10GHz digitally controlled oscillator for UWB impulse radio in 90nm CMOS", 2007 European Solid-State Circuits Conference—(ESSCIRC), Munich, Germany, pp. 484-487.
Di Sieno, et al., "Probe-hosted large area silicon photomultiplier and high-throughput timing electronics for enhanced performance time-domain functional near-infrared spectroscopy", Biomed. Opt. Express 11(11), 6389 (2020).
Dutton, et al., "A Time-Correlated Single-Photon-Counting Sensor with 14GS/s Histogramming Time-to-Digital Converter", 2015 IEEE International Solid-State Circuits Conference ISSCC 2015 / Session 11 / Sensors and Magers for Life Sciences / 11.5.
Dyson, Freeman J. et al., Correlations Between Eigenvalues of a Random Matrix, Commun. Math. Phys. 19, 235-250 (1970) by Springer-Verlag 1970.
Dyson, Freeman J. et al., Statistical Theory of the Energy Levels of Complex Systems. III, J. Math. Phys. 3, 166 (1962); doi: 10.1063/1.1703775.
Fishburn, et al., "Temporal Derivative Distribution Repair (TDDR): A motion correction method for fNIRS", Neuroimage. Jan. 1, 2019; 184: 171-179. doi:10.1016/j.neuroimage.2018.09.025.
Fisher, et al., "A Reconfigurable Single-Photon-Counting Integrating Receiver for Optical Communications", IEEE Journal of Solid-State Circuits, vol. 48, No. 7, Jul. 2013, https://www.researchgate.net/publication/260626902.
Gallivanoni, et al., "Progress in Quenching Circuits for Single Photon Avalanche Diodes", IEEE Transactions on Nuclear Science, vol. 57, No. 6, Dec. 2010.
Gnecchi, et al., "A 1×16 SiPM Array for Automotive 3D Imaging LiDAR Systems."
Harmon, et al., "Compound Semiconductor SPAD Arrays", LightSpin Technologies, http://www.lightspintech.com/publications.html.
Henderson, et al., "A 192 × 128 Time Correlated SPAD Image Sensor in 40-nm CMOS Technology", IEEE Journal of Solid-State Circuits, 2019.
Henderson, et al., "A 256×256 40nm/90nm CMOS 3D-Stacked 120dB Dynamic-Range Reconfigurable Time-Resolved SPAD Imager", 2019 IEEE International Solid- State Circuits Conference—(ISSCC), San Francisco, CA, USA, 2019, pp. 106-108. doi: 10.1109/ISSCC.2019.8662355.
Huppert, et al., "HomER: a review of time-series analysis methods for near-infrared spectroscopy of the brain", Appl. Opt. 48(10), D280 (2009).
Kienle, et al., "Improved solutions of the steady-state and the time-resolved diffusion equations for reflectance from a semi-infinite turbid medium", J. Opt. Soc. Am. A 14(1), 246 (1997).
Kikkawa, Ayumi et al., Random Matrix Analysis for Gene Interaction Networks in Cancer Cells, Scientific Reports (2018) 8:10607 DOI:10.1038/s41598-018-28954-1.
Konugolu, et al., "Broadband (600-1350 nm) Time-Resolved Diffuse Optical Spectrometer for Clinical Use", IEEE Journal of Selected Topics in Quantum Electronics, vol. 22, No. 3, May/Jun. 2016.
Acerenza, et al.,"Wearable and wireless time-domain near-infrared spectroscopy system for brain and muscle hemodynamic monitoring", Biomed. Opt. Express 11(10), 5934 (2020).
Lange, et al., "Clinical Brain Monitoring with Time Domain Nirs: A Review and Future Perspectives", Applied Sciences 9(8), 1612 (2019).
Lange, et al., "Maestros: A Multiwavelength Time-Domain NIRS System to Monitor Changes in Oxygenation and Oxidation State of Cytochrome-C-Oxidase", IEEE J. Select. Topics Quantum Electron. 25(1), 1-12 (2019).
Lee, et al., "High-Performance Back-Illuminated Three-Dimensional Stacked Single-Photon Avalanche Diode Implemented in 45-nm CMOS Technology", IEEE Journal of Selected Topics in Quantum Electronics 6, 1-9 (2018).
Mandai, et al., "A 4 × 4 × 416 digital SiPM array with 192 TDCs for multiple high-resolution timestamp acquisition", 2013 JINST 8 P05024.

(56) References Cited

OTHER PUBLICATIONS

Martelli, et al., "Optimal estimation reconstruction of the optical properties of a two-layered tissue phantom from time-resolved single-distance measurements", Journal of Biomedical Optics 20(11), 115001 (Nov. 2015).
Maruyama, et al.,"A 1024 × 8, 700-ps Time-Gated SPAD Line Sensor for Planetary Surface Exploration With Laser Raman Spectroscopy and Libs", IEEE Journal of Solid-State Circuits, vol. 49, No. 1, Jan. 2014.
Mita, et al., "High-Speed and Compact Quenching Circuit for Single-Photon Avalanche Diodes", IEEE Transactions on Instrumentation and Measurement, vol. 57, No. 3, Mar. 2008. pp. 543-547.
Mora, et al., "Fast silicon photomultiplier improves signal harvesting and reduces complexity in time-domain diffuse optics", Opt. Express 23(11), 13937 (2015).
Mora, et al., "Fast-Gated Single-Photon Avalanche Diode for Wide Dynamic Range Near Infrared Spectroscopy", IEEE Journal of Selected Topics in Quantum Electronics, vol. 16, No. 4, pp. 1023-1030, Jul./Aug. 2010.
Parmesan, et al., "A 256 × 256 SPAD array with in-pixel Time to Amplitude Conversion for Fluorescence Lifetime Imaging Microscopy", 2015.
Pifferi, et al., "Performance assessment of photon migration instruments: the MEDPHOT protocol", Applied Optics, 44(11), 2104-2114.
Prahl, et al., "Optical Absorption of Hemoglobin", http://omlc.ogi.edu/spectra/hemoglobin/index.html.
Puszka, et al.,"Time-resolved diffuse optical tomography using fast-gated single-photon avalanche diodes", Biomedical optics express, 2013, vol. 4, No. 8, pp. 1351-1365 (Year: 2013).
Re, et al., "Multi-channel medical device for time domain functional near infrared spectroscopy based on wavelength space multiplexing", Biomed. Opt. Express 4(10), 2231 (2013).
Renna, et al., "Eight-Wavelength, Dual Detection Channel Instrument for Near-Infrared Time-Resolved Diffuse Optical Spectroscopy", IEEE J. Select. Topics Quantum Electron. 25(1), 1-11 (2019).
Richardson, et al., "A 32×32 50ps resolution 10 bit time to digital converter array in 130nm CMOS for time correlated imaging", CICC 2009 Proceedings of the IEEE 2009 Custom Integrated Circuits Conference. IEEE Society, San Jose, U.S.A., pp. 77-80, CiCC 2009, San Jose, U.S.A., Sep. 13, 2009. https://doi.org/doi:10.1109/CICC.2009.5280890.
Takai, et al., "Single-Photon Avalanche Diode with Enhanced NIR-Sensitivity for Automotive LIDAR Systems", Sensors, 2016, 16(4): 459, pp. 1-9 (Year: 2016).
Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680, Oct. 29, 2018.
Blutman, et al., "A 0.1 pJ Freeze Vernier Time-to-Digital Converter in 65nm CMOS", 2014 International Symposium on Circuits and Systems (ISCAS), Melbourne, Australia, Oct. 29, 2018.
De Heyn, et al., "A fast start-up 3GHZ-10GHz digitally controlled oscillator for UWB impulse radio in 90nm CMOS", 2007 European Solid-State Circuits Conference—(ESSCIRC), Munich, Germany, pp. 484-487, Sep. 11-13, 2007.

Dutton, et al., "A Time-Correlated Single-Photon-Counting Sensor with 14GS/s Histogramming Time-to-Digital Converter", 2015 IEEE International Solid-State Circuits Conference ISSCC 2015 / Session 11 / Sensors and Imagers for Life Sciences / 11.5, Feb. 22-26, 2015.
Gnecchi, et al., "A 1×16 SiPM Array for Automotive 3D Imaging LiDAR Systems.", *Proceedings of the 2017 International Image Sensor Workshop (IISW)*, Hiroshima, Japan (2017).
Harmon, et al., "Compound Semiconductor SPAD Arrays", LightSpin Technologies, http://www.lightspintech.com/publications.html (2013).
Lacerenza, et al., "Wearable and wireless time-domain near-infrared spectroscopy system for brain and muscle hemodynamic monitoring", Biomed. Opt. Express 11(10), 5934 (2020).
Mandai, et al., "A 4 × 4 × 416 digital SiPM array with 192 TDCs for multiple high-resolution timestamp acquisition", 2013 JINST 8 PO5024, May 31, 2013.
Parmesan, et al., "A 256 × 256 SPAD array with in-pixel Time to Amplitude Conversion for Fluorescence Lifetime Imaging Microscopy", *Memory* 900.M4, 2015.
Pifferi, et al., "Performance assessment of photon migration instruments: the MEDPHOT protocol", Applied Optics, 44(11), 2104-2114 (2005).
Prahl, et al., "Optical Absorption of Hemoglobin", http://omlc.ogi.edu/spectra/hemoglobin/index.html (1999).
Torricelli, et al., "Time domain functional NIRS imaging for human brain mapping", NeuroImage 85, 28-50 (2014).
Vergara, Victor M. et al., A Method to Assess Randomness of Functional Connectivity Matrices, J. Neurosci Methods. Jun. 1, 2018; 303: 146-158. doi:10.1016/j.jneumeth.2018.03.015.
Wabnitz, et al., "Depth-selective data analysis for time-domain fNIRS: moments vs. time windows", Biomed. Opt. Express 11(8), 4224 (2020).
Wabnitz, et al., "Performance assessment of time-domain optical brain imagers, part 1: basic instrumental performance protocol", Journal of Biomedical Optics 19(8), 086010 (Aug. 2014).
Wabnitz, et al., "Performance assessment of time-domain optical brain imagers, part 2: nEUROPt protocol", Journal of Biomedical Optics 19(8), 086012 (Aug. 2014).
Wojtkiewicz, et al., "Self-calibrating time-resolved near infrared spectroscopy", Biomed. Opt. Express 10(5), 2657 (2019).
Zabronen, Anton et al., Financial Applications of Random Matrix Theory: A Short Review, The Oxford Handbook of Random Matrix Theory. Print Publ: Sep. 2015. Online Publ: Aug. 2018. DOI: 10.1093/oxfordhb/9780198744191.013.40.
Zhang, et al., "A CMOS SPAD Imager with Collision Detection and 128 Dynamically Reallocating TDCs for Single- Photon Counting and 3D Time-of-Flight Imaging", Sensors (Basel, Switzerland), 18(11), 4016. doi:10.3390/s18114016.
Zucchelli, et al.,"Method for the discrimination of superficial and deep absorption variations by time domain fNIRS", 2013 OSA Dec. 1, 2013 | vol. 4, No. 12 | DOI:10.1364/BOE.4.002893 | Biomedical Optics Express 2893.
Torricelli, et al., "Time domain functional NIRS imaging for human brain mapping", NeuroImage 85, 28-50 (2014).
Zhang, et al., "A CMOS SPAD Imager with Collision Detection and 128 Dynamically Reallocating TDCs for Single- Photon Counting and 3D Time-of-Flight Imaging", Sensors (Basel, Switzerland), 18(11), 4016. doi: 10.3390/s18114016 Nov. 17, 2018.

* cited by examiner

SYSTEMS AND METHODS FOR NOISE REMOVAL IN AN OPTICAL MEASUREMENT SYSTEM

RELATED APPLICATIONS

The present application claims priority under 35 U.S.C. § 119(e) to U.S. Provisional Patent Application No. 63/138,159, filed on Jan. 15, 2021, and to U.S. Provisional Patent Application No. 63/015,012, filed on Apr. 24, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

However, the light pulses must travel through other layers of tissue (e.g., scalp, skull, cerebrospinal fluid (CSF), etc.) to reach the brain. These other layers may also respond to the light pulses, introducing noise into the histogram. Further, noise may be introduced by defects and/or impurities in components of an optical measurement system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
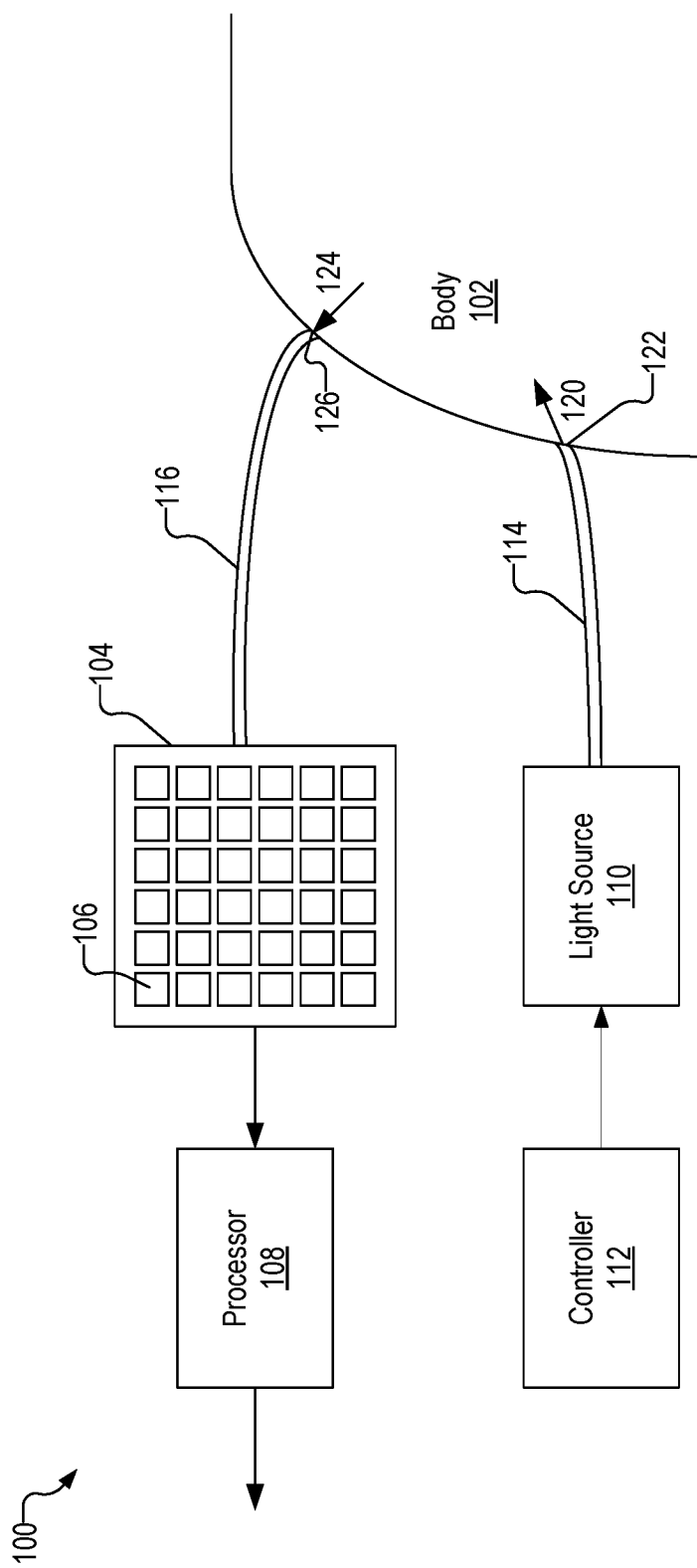
FIG. 1 shows an exemplary optical measurement system.

In accordance with the systems and methods described herein, an optical measurement system may include a light source configured to emit light directed at a target within a user. The optical measurement system may further include a detector configured to detect photon arrival times for photons of the light after the light is scattered by the target. The optical measurement system may further include a processing unit configured to determine, based on the photon arrival times, histogram data associated with the target, the histogram data including noise. The processing unit may be further configured to determine, based on the photon arrival times, a random matrix corresponding to the photon arrival times. The processing unit may be further configured to determine, based on the random matrix, a noise distribution representing a distribution of the noise within the histogram data. The processing unit may be further configured to generate clean histogram data using the noise distribution to filter at least a portion of the noise from the histogram data.

For example, an optical measurement system as described herein may be used to measure a neural activity response of a brain of a user to light. As described herein, the brain is covered by other layers of tissue, which may include the scalp, the skull, CSF, and/or other types of tissue. Because the light passes through these other layers before reaching the brain, these other layers may introduce noise into the measured neural activity response of a brain. Further, the optical measurement system may introduce noise into the measured neural activity response of a brain due to process variations, defects, impurities, etc. in components of the optical measurement system, such as photodetectors.

To remove (e.g., by filtering, reducing, and/or eliminating) the noise, a processing unit may apply random matrix theory (RMT) to model noise that may be characterized by random interactions or correlations in histogram data. Portions of the histogram data that correspond to such a modeled noise distribution may be removed to generate clean histogram data that corresponds to non-random, meaningful signal on the measured neural activity response of a brain. The clean histogram data may be used to determine various types of information associated with the brain and/or a user.

For example, the clean histogram data may be used to infer or otherwise detect neural activity within the brain. In some examples, such neural activity may be used to make behavioral and mental state analysis, awareness and predictions for the user. Accordingly, using clean histogram data as opposed to histogram data that includes noise for such determinations may result in more accurate and useful metrics and predictions for the user.

Mental states described herein refer to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Further, the clean histogram data may be of a reduced dimensionality compared to the histogram data that includes noise. Thus, the clean histogram data may require fewer resources to process, transmit, and/or store than the histogram data that includes noise.

These and other advantages and benefits of the present systems and methods are described more fully herein.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser. No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain Digital Optical Tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diodes (mLEDs), and/or any other suitable laser or light source. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by an arrow 120, the light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
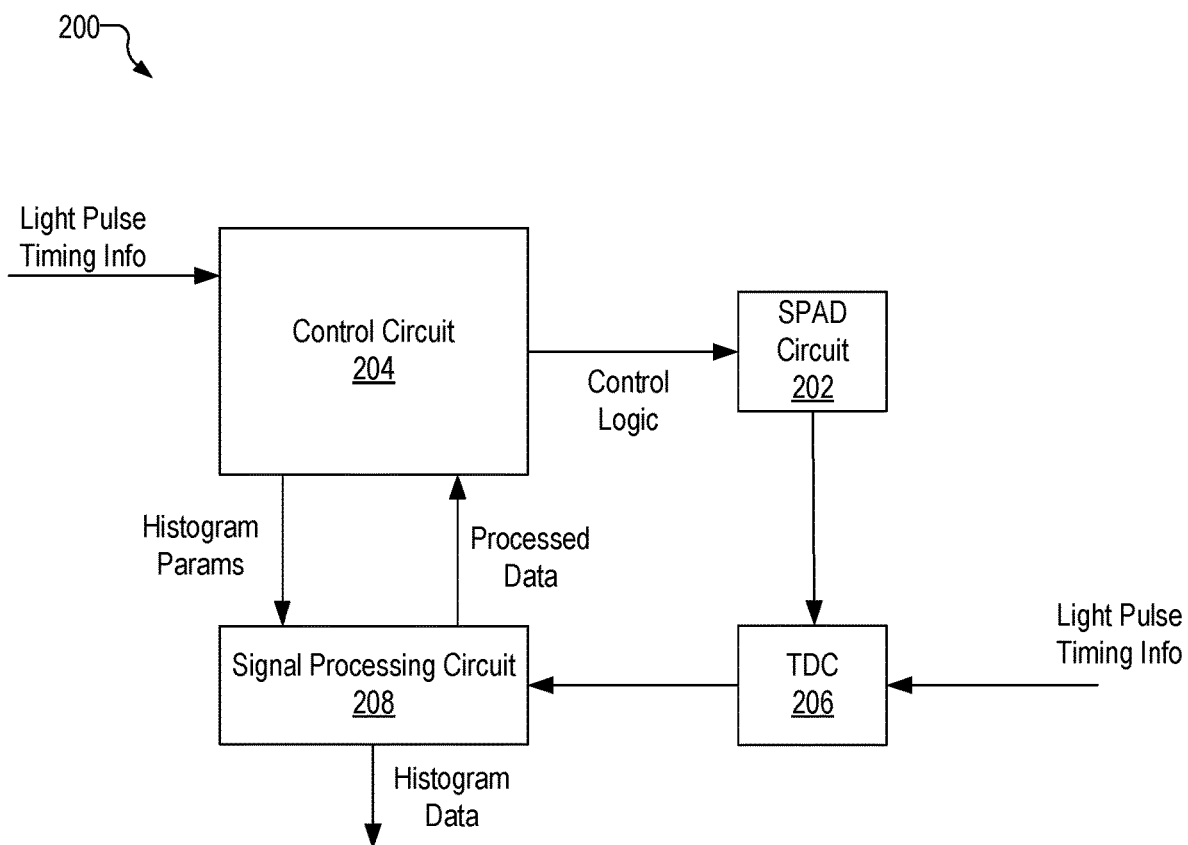
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 may include a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may be implemented by an active voltage source, a capacitor that is pre-charged with a bias voltage before a command is provided to arm the SPAD, and/or in any other suitable manner.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control an arming and a disarming of a SPAD included in SPAD circuit 202. Control circuit 204 may also control a programmable gate width, which specifies how long the SPAD is kept in an armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Likewise, a single control circuit 204 and a single signal processing circuit 208 may be provided for one or more photodetectors 106 and/or TDCs 206.

Figure 3:
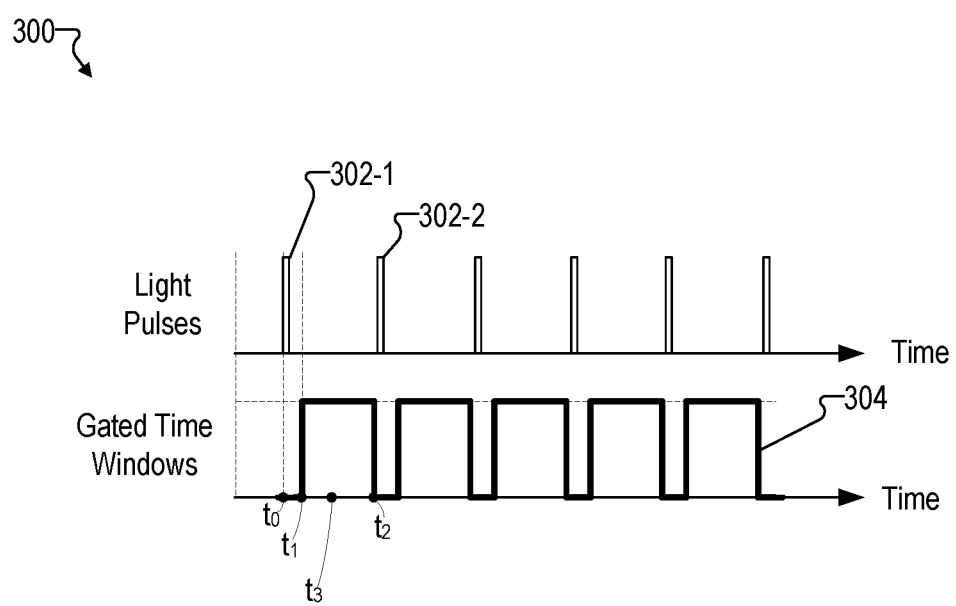
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON (i.e., armed) to detect photons. Referring to light pulse 302-1, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

As described herein, the systems, circuits, and methods described herein may obviate the need for the gated time windows described in connection with FIG. 3, thereby obviating the need for fast gating circuitry to be included in optical measurement system 100.

Figure 4:
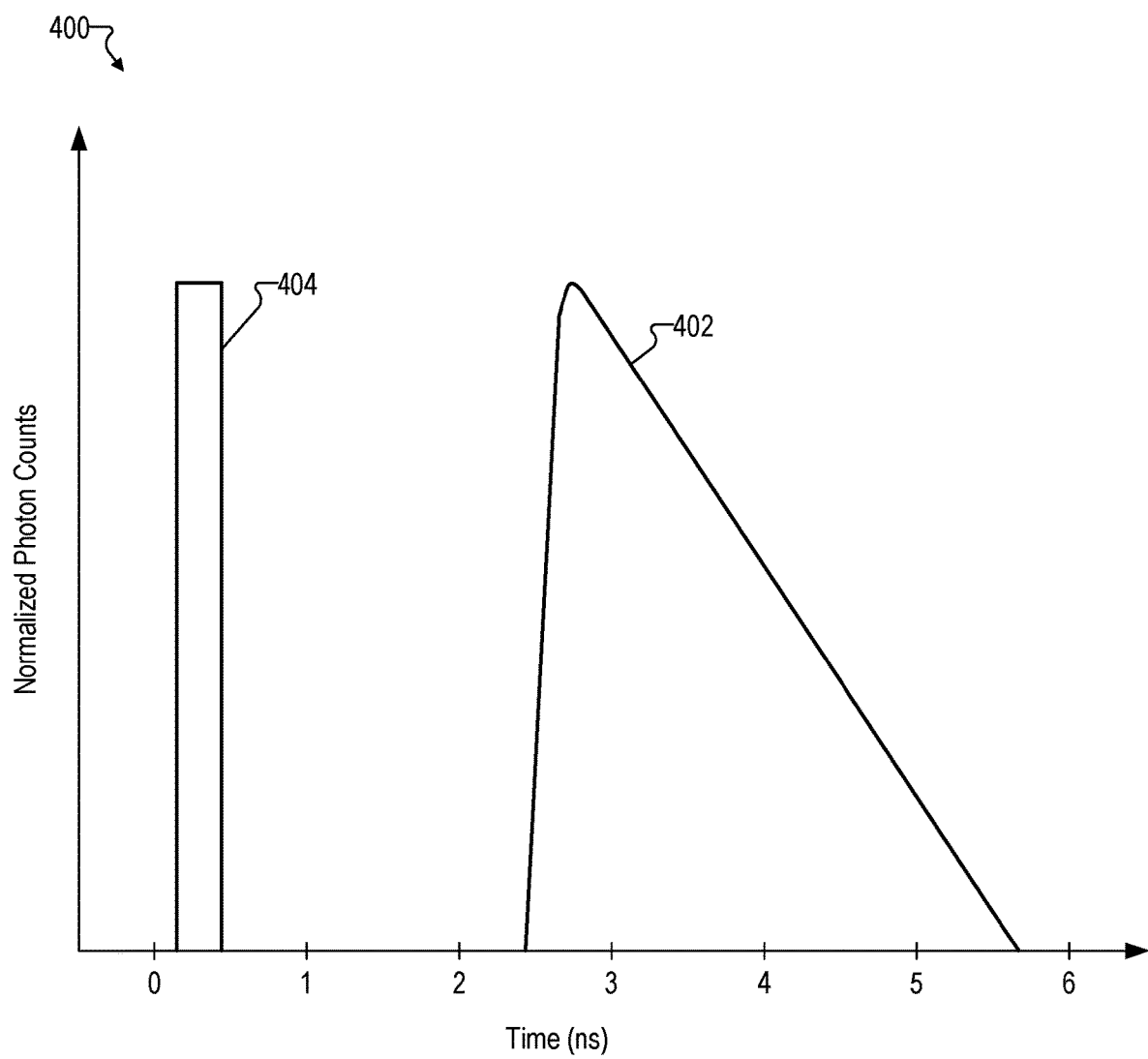
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included in a non-invasive wearable device (e.g., a headpiece) that a user may wear to perform one or more diagnostic, imaging, analytical, and/or consumer-related operations.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
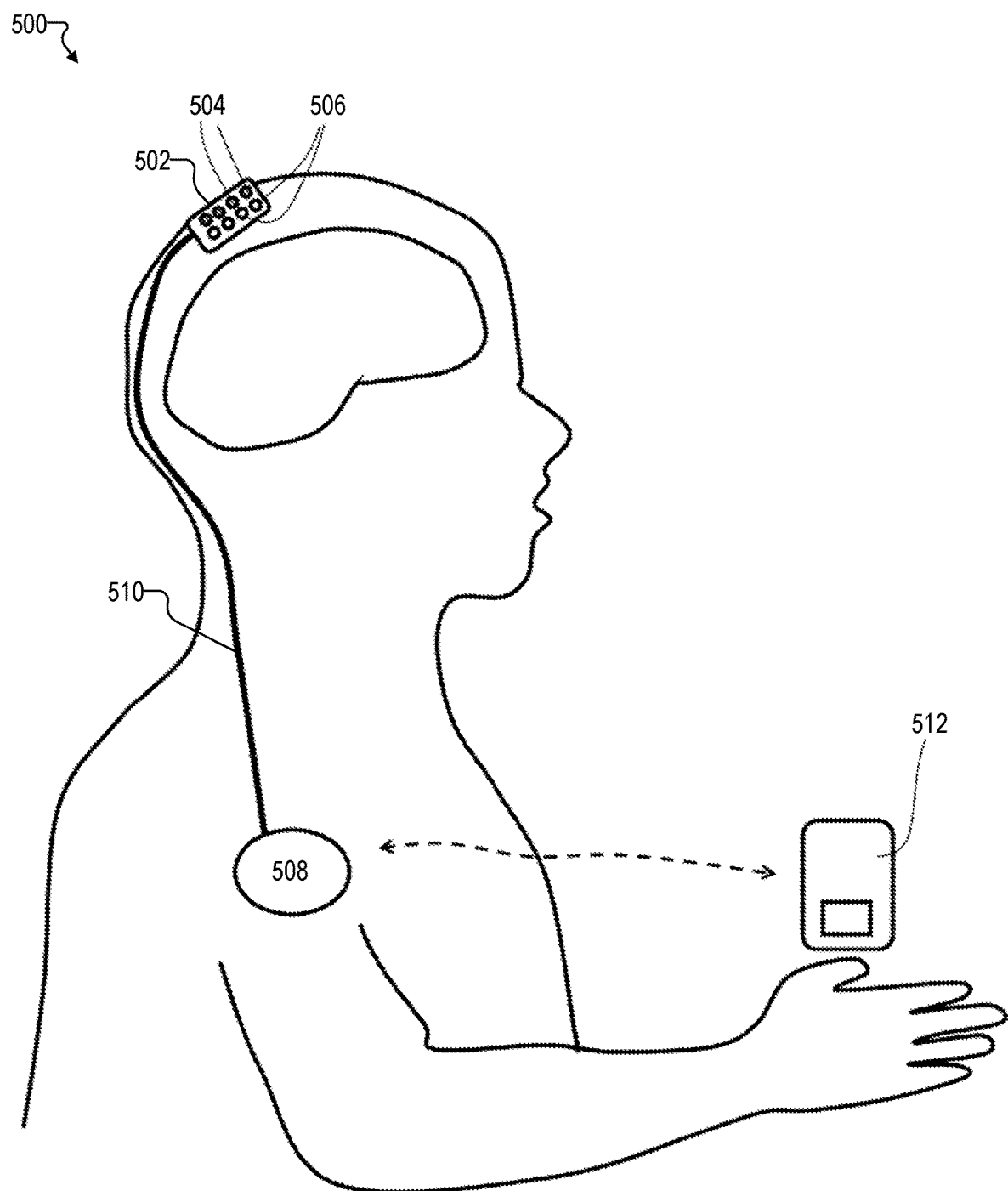
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detectors 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Figure 6:
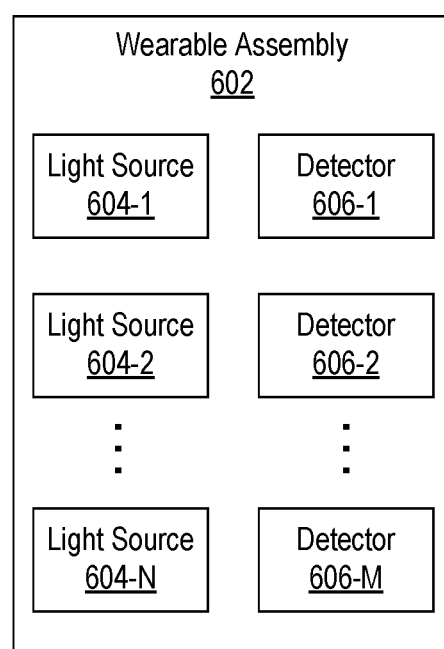
FIG. 6 shows an exemplary optical measurement system.

FIG. 6 shows an exemplary optical measurement system 600 in accordance with the principles described herein. Optical measurement system 600 may be an implementation of optical measurement system 100 and, as shown, includes a wearable assembly 602, which includes N light sources 604 (e.g., light sources 604-1 through 604-N) and M detectors 606 (e.g., detectors 606-1 through 606-M). Optical measurement system 600 may include any of the other components of optical measurement system 100 as may serve a particular implementation. N and M may each be any suitable value (i.e., there may be any number of light sources 604 and detectors 606 included in optical measurement system 600 as may serve a particular implementation).

Light sources 604 are each configured to emit light (e.g., a sequence of light pulses) and may be implemented by any of the light sources described herein. Detectors 606 may each be configured to detect arrival times for photons of the light emitted by one or more light sources 604 after the light is scattered by the target. For example, a detector 606 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector).

Wearable assembly 602 may be implemented by any of the wearable devices, modular assemblies, and/or wearable units described herein. For example, wearable assembly 602 may be implemented by a wearable device (e.g., headgear) configured to be worn on a user's head. Wearable assembly 602 may additionally or alternatively be configured to be worn on any other part of a user's body.

Optical measurement system 600 may be modular in that one or more components of optical measurement system 600 may be removed, changed out, or otherwise modified as may serve a particular implementation. As such, optical measurement system 600 may be configured to conform to three-dimensional surface geometries, such as a user's head. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Feb. 16, 2021, and U.S. patent application Ser. No. 17/176,560, filed Feb. 16, 2021, which applications are incorporated herein by reference in their respective entireties.

Figure 7:
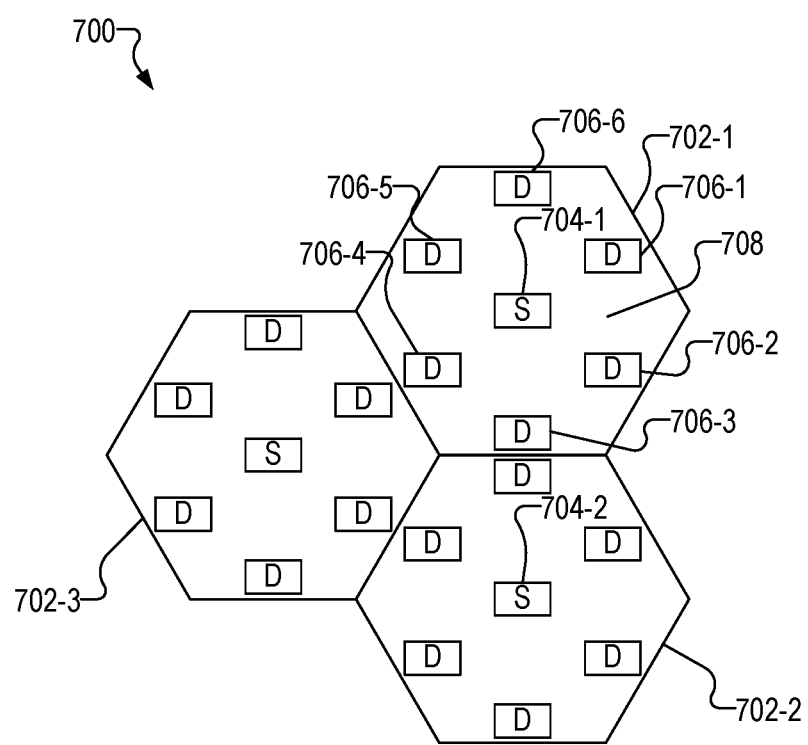
FIG. 7 shows an illustrative modular assembly.

FIG. 7 shows an illustrative modular assembly 700 that may implement optical measurement system 600. Modular assembly 700 is illustrative of the many different implementations of optical measurement system 600 that may be realized in accordance with the principles described herein.

As shown, modular assembly 700 includes a plurality of modules 702 (e.g., modules 702-1 through 702-3). While three modules 702 are shown to be included in modular assembly 700, in alternative configurations, any number of modules 702 (e.g., a single module up to sixteen or more modules) may be included in modular assembly 700.

Each module 702 includes a light source (e.g., light source 704-1 of module 702-1 and light source 704-2 of module 702-2) and a plurality of detectors (e.g., detectors 706-1 through 706-6 of module 702-1). In the particular implementation shown in FIG. 7, each module 702 includes a single light source and six detectors. Each light source is labeled "S" and each detector is labeled "D".

Each light source depicted in FIG. 7 may be implemented by one or more light sources similar to light source 110 and may be configured to emit light directed at a target (e.g., the brain).

Each light source depicted in FIG. 7 may be located at a center region of a surface of the light source's corresponding module. For example, light source 704-1 is located at a center region of a surface 708 of module 702-1. In alternative implementations, a light source of a module may be located away from a center region of the module.

Each detector depicted in FIG. 7 may implement or be similar to detector 104 and may include a plurality of photodetectors (e.g., SPADs) as well as other circuitry (e.g., TDCs), and may be configured to detect arrival times for photons of the light emitted by one or more light sources after the light is scattered by the target.

The detectors of a module may be distributed around the light source of the module. For example, detectors 706 of module 702-1 are distributed around light source 704-1 on surface 708 of module 702-1. In this configuration, detectors 706 may be configured to detect photon arrival times for photons included in light pulses emitted by light source 704-1. In some examples, one or more detectors 706 may be close enough to other light sources to detect photon arrival times for photons included in light pulses emitted by the other light sources. For example, because detector 706-3 is adjacent to module 702-2, detector 706-3 may be configured to detect photon arrival times for photons included in light pulses emitted by light source 704-2 (in addition to detecting photon arrival times for photons included in light pulses emitted by light source 704-1).

In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling) information about the detected signals. Detectors of a module may be alternatively disposed on the module as may serve a particular implementation.

Figure 8A:
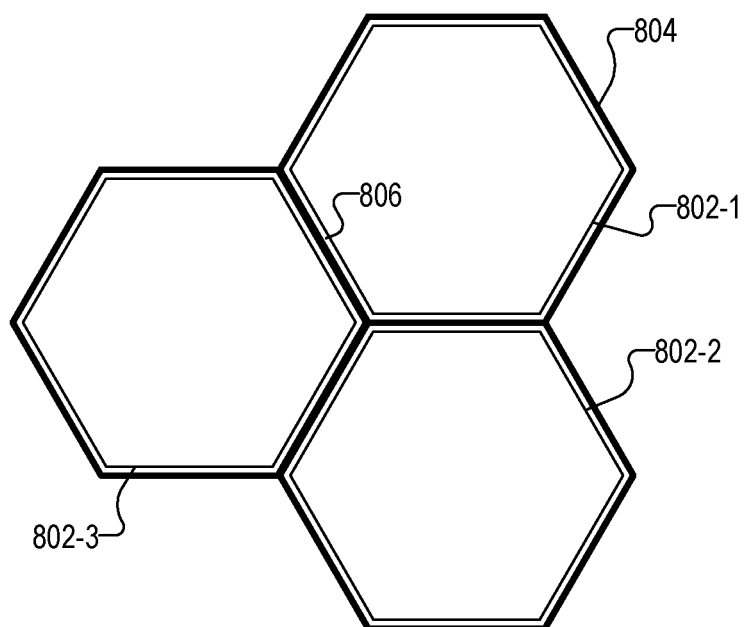
FIGS. 8A-8B show an exemplary implementation of the modular assembly of FIG. 7.
Figure 8B:
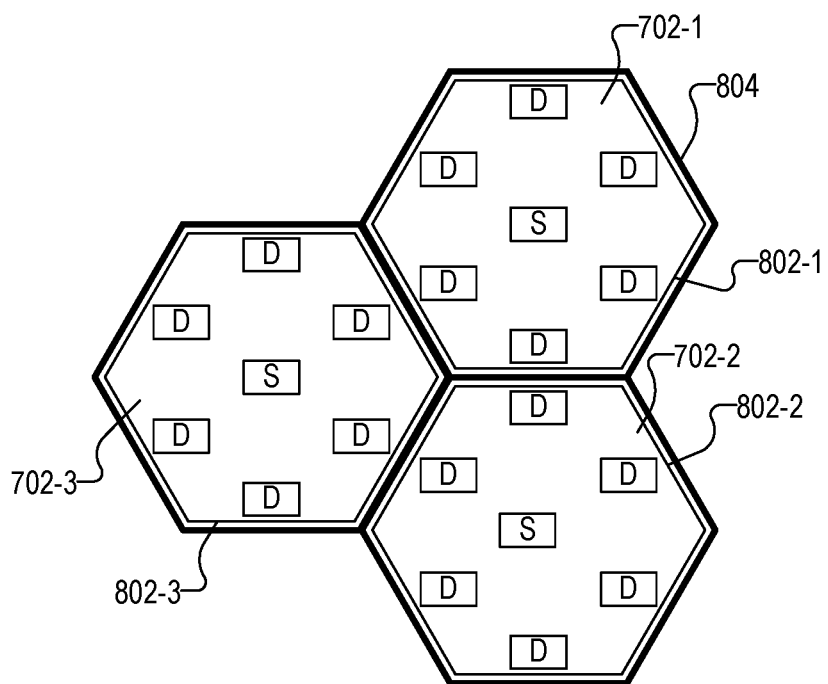

In FIG. 7, modules 702 are shown to be adjacent to and touching one another. Modules 702 may alternatively be spaced apart from one another. For example, FIGS. 8A-8B show an exemplary implementation of modular assembly 700 in which modules 702 are configured to be inserted into individual slots 802 (e.g., slots 802-1 through 802-3, also referred to as cutouts) of a wearable assembly 804. In particular, FIG. 8A shows the individual slots 802 of the wearable assembly 804 before modules 702 have been inserted into respective slots 802, and FIG. 8B shows wearable assembly 804 with individual modules 702 inserted into respective individual slots 802.

Wearable assembly 804 may implement wearable assembly 602 and may be configured as headgear and/or any other type of device configured to be worn by a user.

As shown in FIG. 8A, each slot 802 is surrounded by a wall (e.g., wall 806) such that when modules 702 are inserted into their respective individual slots 802, the walls physically separate modules 702 one from another. In alternative embodiments, a module (e.g., module 702-1) may be in at least partial physical contact with a neighboring module (e.g., module 702-2).

Each of the modules described herein may be inserted into appropriately shaped slots or cutouts of a wearable assembly, as described in connection with FIGS. 8A-8B. However, for ease of explanation, such wearable assemblies are not shown in the figures.

As shown in FIGS. 7 and 8B, modules 702 may have a hexagonal shape. Modules 702 may alternatively have any other suitable geometry (e.g., in the shape of a pentagon, octagon, square, rectangular, circular, triangular, free-form, etc.).

Figure 9:
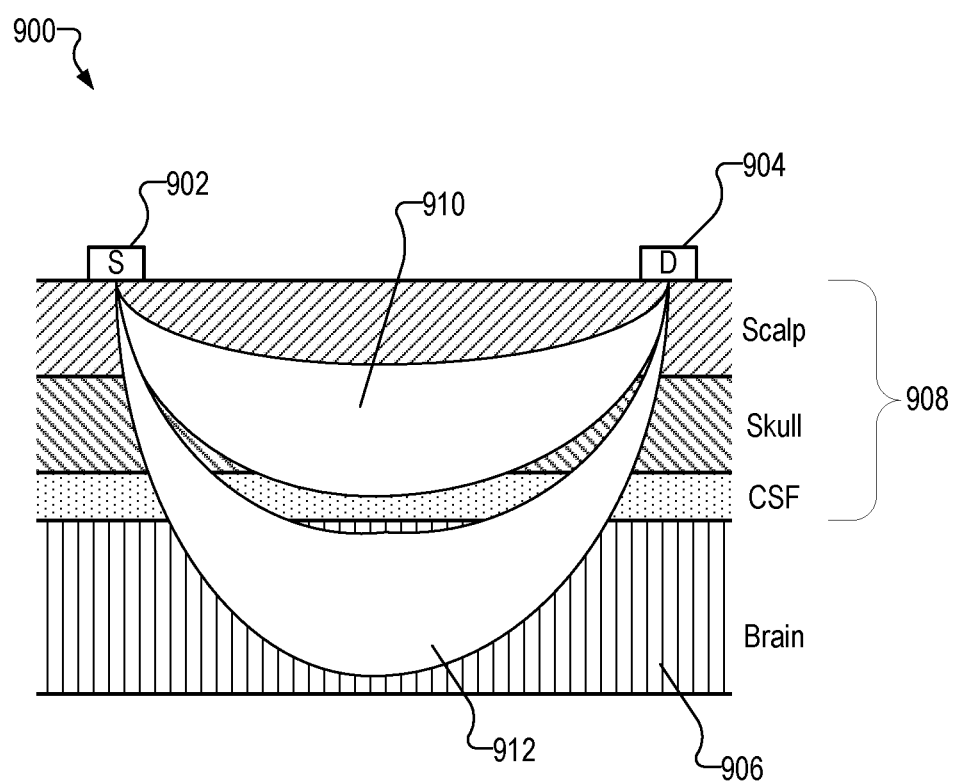
FIG. 9 shows an exemplary portion of an optical measurement system.

FIG. 9 shows an exemplary configuration 900 of a portion of an optical measurement system (e.g., optical measurement system 100). Configuration 900 shows a light source 902 (e.g., an implementation of light source 110) and a detector 904 (e.g., an implementation of detector 104). Light source 902 may be configured to emit light directed at a target 906. In the example of FIG. 9, target 906 is the brain of a user. Target 906 may alternatively be any other area within the body of the user.

Light source 902 may emit light directed at target 906. Detector 904 may include photodetectors (e.g., photodetectors 106) that are configured to detect photons from the light emitted by light source 902 after the light is scattered. Some of the photons may be scattered by layers 908 of tissue and/or bodily fluids other than target 906 and exit the body before reaching target 906. For example, an optical path region 910 shows possible light paths of such photons scattered by layers 908 and exiting the body before reaching the brain. Others of the photons may pass through layers 908, where they are scattered by target 906 before exiting the body. For example, an optical path region 912 shows possible light paths of the photons scattered by target 906. Thus, some of photodetectors 106 may detect the photons of optical path region 910, while others of photodetectors 106 may detect the photons of optical path region 912.

Detector 904 may output signals based on times that photodetectors 106 detect photons. For instance, detector 904 may include one or more TDCs that record and output timestamp symbols (or any other suitable representation of time information) that correspond to the times that photodetectors 106 detect photons. Based on the timestamp symbols, optical measurement system 100 may generate histogram data (e.g., a TPSF, etc.). However, photons of optical path region 910 detected by photodetectors 106 may introduce noise into histogram data, as the histogram data of interest may be based on photons of optical path region 912, scattered by target 906.

Figure 10:
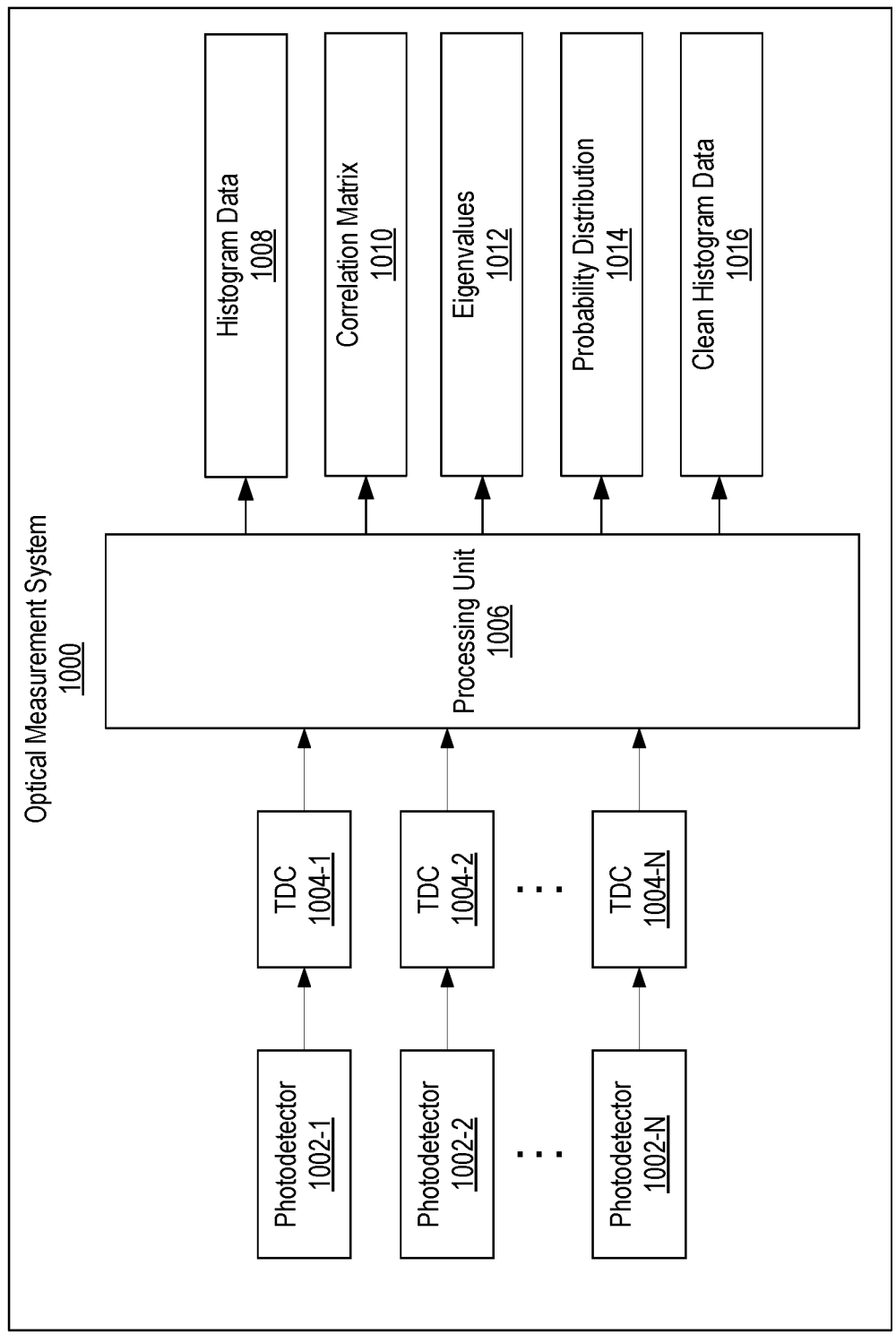
FIG. 10 shows an exemplary optical measurement system.

FIG. 10 shows an exemplary optical measurement system 1000 that may be similar to and/or implement any of the optical measurement systems described herein. As shown, optical measurement system 1000 includes a plurality of photodetectors 1002 (e.g., photodetectors 1002-1 through 1002-N), a plurality of TDCs 1004 (e.g., TDCs 1004-1 through 1004-N), and a processing unit 1006. Each of these elements may be similar to the elements described herein.

For example, photodetectors 1002 may be implemented by any of the photodetectors described herein and may be configured to detect photons of light after the light is scattered by the target and/or other layers of tissue. TDCs 1004 may be implemented by any of the TDCs described herein and may be configured to record timestamp symbols representative of when the photons are detected by photodetectors 1002.

Processing unit 1006 may be implemented by processor 108, controller 112, control circuit 204, and/or any other suitable processing and/or computing device or circuit. An exemplary implementation of processing unit 1006 is described herein.

As shown, processing unit 1006 may be configured to receive output signals from TDCs 1004 and perform, based on the output signals, one or more operations. For example, as described herein, processing unit 1006 may be configured to generate histogram data based on the output signals and remove noise from the histogram data. The output signals may include data representative of recorded timestamp symbols, as described herein.

As shown, processing unit 1006 may generate histogram data 1008, which may be based on timestamp symbols representing arrival times of photons at photodetectors 1002. Histogram data 1008 may include data associated with a target (e.g., target 906), but may also include noise. Noise may include any input that is not based on characteristics being measured in target 906. For instance, noise may include arrival times of photons reflected off of layers of tissue other than target 906, (e.g., layers 908). Noise may also include arrival times of photons reflected off of target 906 but unrelated to a characteristic being measured (e.g., characteristics such as a neurological signal corresponding to a task). For instance, such unrelated signals may be a product of physiological processes (e.g., heartbeat, etc.) and/or movement by the user. Noise may also include outputs of photodetectors 1002 and/or TDCs 1004 due to process variation, device impurities, defects, etc.

Processing unit 1006 may be configured to filter at least a portion of the noise included in histogram data 1008 using principles of random matrix theory (RMT). For instance, processing unit 1006 may generate a histogram data matrix (not shown in FIG. 10) using histogram data 1008. The histogram data matrix may have a size of n columns and m rows. The n columns may include a column for each of the time bins in histogram data 1008. The m rows may include a row for each occurrence of a light pulse directed at target 906. The m rows may also include rows for each photodetector 1002 (e.g., m may equal N times Q, where N is the number of photodetectors 1002 and Q is the number of light pulses).

Processing unit 1006 may determine a correlation matrix 1010 based on the histogram data matrix. Correlation matrix 1010 may be an n by n matrix of pairwise correlations between the n time bins across the m rows of the histogram data matrix. As correlation matrix 1010 may have a same mean and variance as the histogram data matrix (and consequently, histogram data 1008), processing unit 1006 may use correlation matrix 1010 as a random matrix for modeling the noise in histogram data 1008 using RMT.

Processing unit 1006 may determine eigenvalues 1012 of correlation matrix 1010. Processing unit 1006 may determine eigenvalues 1012 in any suitable manner. Processing unit 1006 may further determine one or more probability distributions 1014 based on eigenvalues 1012. For example, probability distributions 1014 may include a modeled noise distribution of histogram data 1008 as further described herein. Based on the noise distribution, processing unit 1006 may filter at least a portion of the noise in histogram data 1008 to generate clean histogram data 1016.

Figure 11:
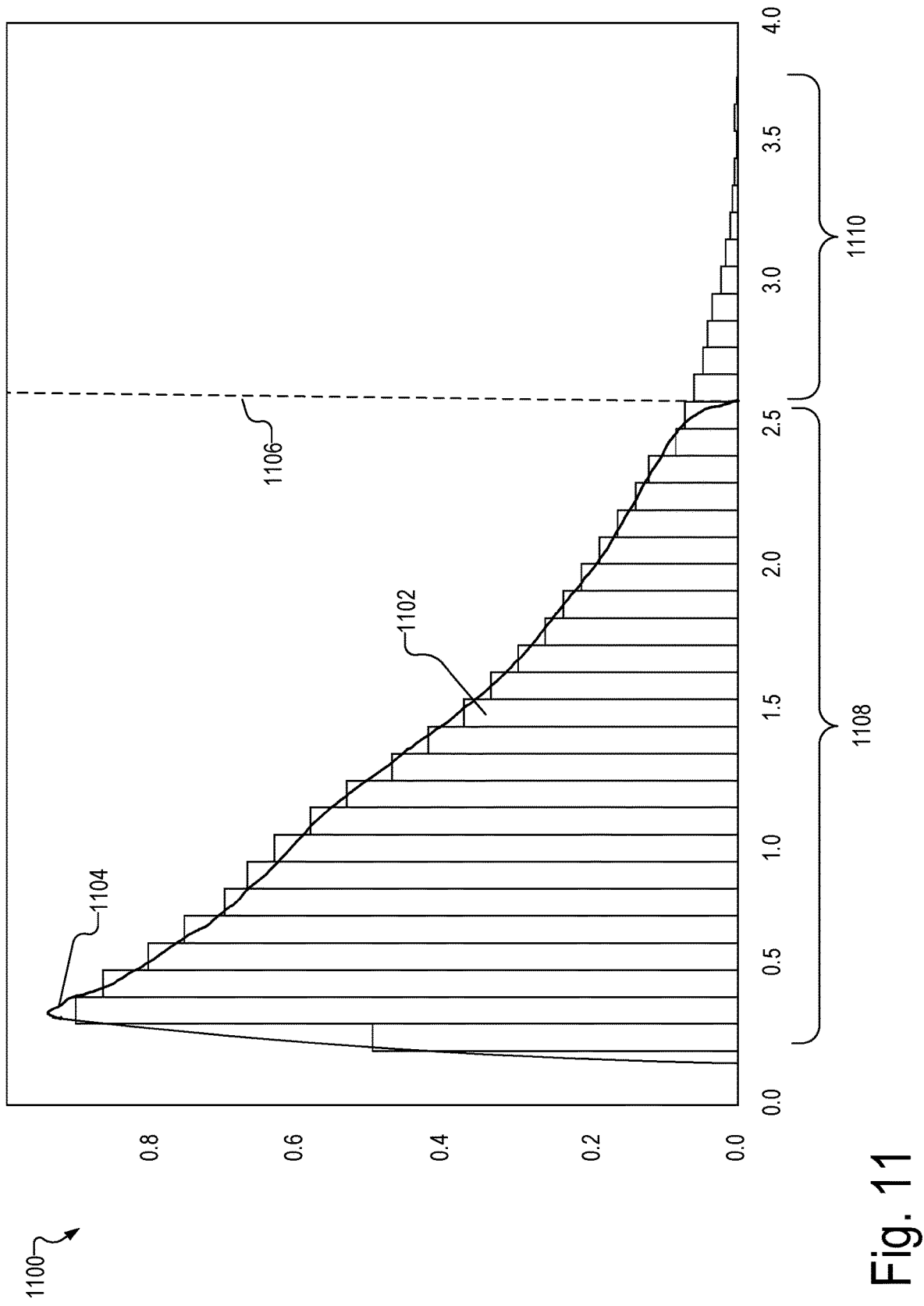
FIG. 11 shows an exemplary graph for noise removal.

FIG. 11 illustrates an exemplary graph 1100 showing histogram data (e.g., histogram data 1008) based on arrival times of photons scattered by a target (e.g., target 906) as measured by an optical measurement system (e.g., optical measurement system 1000). Graph 1100 further shows a noise distribution (e.g., a probability distribution 1014), which may be based on a random matrix (e.g., correlation matrix 1010) corresponding to the photon arrival times included in histogram data 1008.

For example, graph 1100 includes bars 1102 that depict a normalized distribution of eigenvalues (e.g., eigenvalues 1012) determined based on correlation matrix 1010. Correlation matrix 1010 is determined based on histogram data 1008. Thus, bars 1102 represent eigenvalues 1012 based on histogram data 1008, which includes arrival times of photons scattered by target 906 as well as noise.

Graph 1100 further includes a curve 1104 that depicts the noise distribution determined from correlation matrix 1010 using RMT. For instance, curve 1104 may be determined based on correlation matrix 1010 using a distribution as predicted by a Marchenko-Pastur distribution (or any other suitable distribution that may be applied using RMT). For example, curve 1104 may be determined based on $$P_{rm}(\lambda) = \frac{Q}{2\pi} \frac{\sqrt{(\lambda_+ - \lambda)(\lambda - \lambda_-)}}{\lambda},$$

where $P_{rm}$ is the expected distribution, Q is the number of light pulses, and $\lambda_+$ and $\lambda_-$ are theoretical boundaries of $P_{rm}$.

Curve 1104 may thus represent a theoretical model of random interactions or correlations in histogram data 1008, which may correspond to noise. By filtering out eigenvalues found in the noise distribution range, remaining eigenvalues (e.g., eigenvalues outside boundaries of the Marchenko-Pastur distribution) may represent non-random and therefore meaningful data that may correspond to signals generated by target 906 associated with characteristics being measured. A dashed line 1106 shows a demarcation among bars 1102 between bars 1108 that are found in the noise distribution (e.g., under curve 1104) and bars 1110 that are outside the noise distribution range.

Thus, bars 1108 may represent noise eigenvalues that correspond to noise in histogram data 1008, while bars 1110 may represent signal eigenvalues that correspond to signal in histogram data 1008. Optical measurement system 1000 (e.g., processing unit 1006) may project signal eigenvalues represented by bars 1110 on to an eigenvector subspace to determine signal eigenvectors corresponding to the signal eigenvalues. Processing unit 1006 may generate a clean histogram data matrix based on the signal eigenvectors, resulting in a matrix that includes clean histogram data 1016.

Clean histogram data 1016 may then be used in any suitable manner. For example, processing unit 1006 may further process clean histogram data 1016 to detect neural activity of the user or any other such analysis, such as by using machine learning models, predictions, classifications, etc. Additionally or alternatively, processing unit 1006 may provide clean histogram data 1016 to any other component of optical measurement system 1000 and/or any other system for further processing and/or analysis. As generating clean histogram data 1016 by filtering noise in histogram data 1008 using RMT may include removing a non-trivial or substantial portion of the data (e.g., bars 1108), such processes may also allow for a reduction in a dimensionality of histogram data 1008 to clean histogram data 1016. Such dimensionality reduction may result in a compression of histogram data 1008, which may reduce resources used in processing, transmitting, and/or storing clean histogram data 1016 compared to histogram data 1008.

Processing unit 1006 may be further configured to determine additional probability distributions (e.g., probability distributions 1014), such as distributions that may be used to test and/or verify an applicability of RMT to histogram data 1008. For example, a modeled noise distribution based on RMT may be applicable to histogram data 1008 provided that histogram data 1008 conforms to certain characteristics. For instance, probability distributions 1014 may include a distribution of eigenvector components determined based on correlation matrix 1010. Such a distribution may be used to verify whether the eigenvectors are delocalized. Delocalized eigenvectors would indicate that the noise included in histogram data 1008 is distributed across time bins, as would be expected with random noise, and therefore can be modeled using RMT.

Additionally or alternatively, probability distributions 1014 may include a distribution generated to compare the noise distribution as determined based on correlation matrix 1010 (e.g., curve 1104) to an expected theoretical distribution based on RMT. For example, processing unit 1006 may generate a plurality of fictitious random matrices with values chosen independently and randomly from a distribution with a same mean and variance as correlation matrix 1010. Processing unit 1006 may generate an expected distribution based on the plurality of fictitious random matrices and compare the distribution with curve 1104 to verify that curve 1104 is within a threshold variance of the expected distribution based on the fictitious random matrices.

Additionally or alternatively, probability distributions 1014 may include a cumulative distribution of eigenvalue differences based on curve 1104 and the expected distribution. For instance, eigenvalues 1012 determined based on correlation matrix 1010 may be unfolded, such as with Gaussian broadening or any other suitable algorithm. Processing unit 1006 may determine a cumulative distribution of the unfolded eigenvalues. Processing unit 1006 may also determine expected eigenvalues based on the expected distribution (e.g., based on the plurality of fictitious random matrices). Processing unit 1006 may determine a cumulative distribution of the expected eigenvalues and compare the two cumulative distributions. Such a comparison may provide another indication of the applicability of RMT to histogram data 1008.

Additionally or alternatively, probability distributions 1014 may include a cumulative distribution of eigenvalues, such as a distribution of distances between nearest-neighbor eigenvalues. Processing unit 1006 may determine for some or all of eigenvalues 1012 distances to nearest-neighbor eigenvalues for each respective eigenvalue. Such distances may be compared to distances as would be expected from a theoretical model, such as a Gaussian Symplectic Ensemble, which may be determined using an equation such as $$P_{GSE}(s) = \frac{2^{18}}{3^6 \pi^3} s^4 \exp\left(-\frac{64}{9\pi}s^2\right),$$

where $P_{GSE}(s)$ is the expected distribution for each distance s. Such a comparison may also provide another indication of the applicability of RMT to histogram data 1008.

These probability distributions 1014 for testing the applicability of RMT for histogram data 1008 may be used in any suitable manner. For example, each distribution may have a threshold and/or a combination of distributions may have a combined threshold to determine whether the noise distribution determined based on correlation matrix 1010 is to be used to remove noise from histogram data 1008.

Some or all of probability distributions 1014 may be determined with any suitable frequency. For example, some or all of the distributions for verifying the applicability of RMT may be determined every instance of noise being filtered from a set of histogram data 1008 using RMT, every other instance, every specific number of instances, at random intervals of instances, etc. Further, different probability distributions may be determined at different instances.

Figure 12:
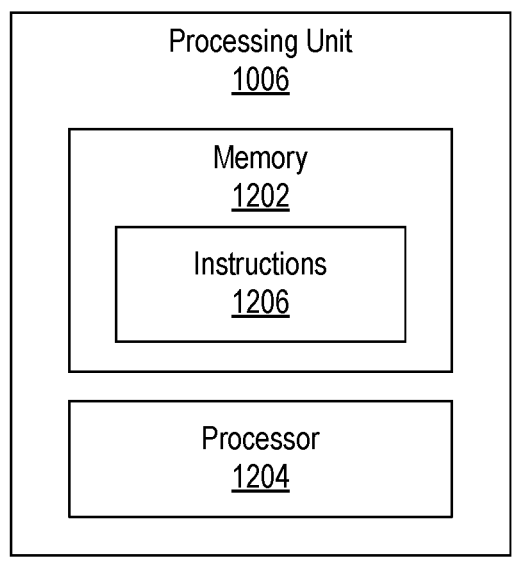
FIG. 12 illustrates an exemplary implementation of a processing unit.

FIG. 12 illustrates an exemplary implementation of processing unit 1006 in which processing unit 1006 includes a memory 1202 and a processor 1204 configured to be selectively and communicatively coupled to one another. In some examples, memory 1202 and processor 1204 may be distributed between multiple devices and/or multiple locations as may serve a particular implementation.

Memory 1202 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1202 may maintain (e.g., store) executable data used by processor 1204 to perform one or more of the operations described herein. For example, memory 1202 may store instructions 1206 that may be executed by processor 1204 to perform any of the operations described herein. Instructions 1206 may be implemented by any suitable application, program (e.g., sound processing program), software, code, and/or other executable data instance. Memory 1202 may also maintain any data received, generated, managed, used, and/or transmitted by processor 1204.

Processor 1204 may be configured to perform (e.g., execute instructions 1206 stored in memory 1202 to perform) various operations described herein. For example, processor 1204 may be configured to perform any of the operations described herein as being performed by processing unit 1006.

In some examples, processing unit 1006 may be included in the same wearable system (e.g., a head-mountable component) that includes photodetectors 1002 and TDCs 1004. Alternatively, processing unit 1006 is not included in the same wearable system that includes photodetectors 1002 and TDCs 1004.

To illustrate, processing unit 1006 may be included in a wearable device separate from a head-mountable component that includes photodetectors 1002 and TDCs 1004. For example, processing unit 1006 may be included in a wearable device configured to be worn off the head while the head-mountable component is worn on the head. In these examples, one or more communication interfaces (e.g., cables, wireless interfaces, etc.) may be used to facilitate communication between the head-mountable component and the separate wearable device.

Additionally or alternatively, processing unit 1006 may be remote from the user (i.e., not worn by the user). For example, processing unit 1006 may be implemented by a stand-alone computing device communicatively coupled the head-mountable component by way of one or more communication interfaces (e.g., cables, wireless interfaces, etc.).

FIGS. 13-18 illustrate embodiments of a wearable device 1300 that includes elements of the optical detection systems described herein. In particular, the wearable devices 1300 shown in FIGS. 13-20 include a plurality of modules 1302, similar to the modules described herein. For example, each module 1302 may include a light source (e.g., light source 704-1) and a plurality of detectors (e.g., detectors 706-1 through 706-6). The wearable devices 1300 may each also include a controller (e.g., controller 112) and a processor (e.g., processor 108) and/or be communicatively connected to a controller and processor. In general, wearable device 1300 may be implemented by any suitable headgear and/or clothing article configured to be worn by a user. The headgear and/or clothing article may include batteries, cables, and/or other peripherals for the components of the optical measurement systems described herein.

Figure 13:
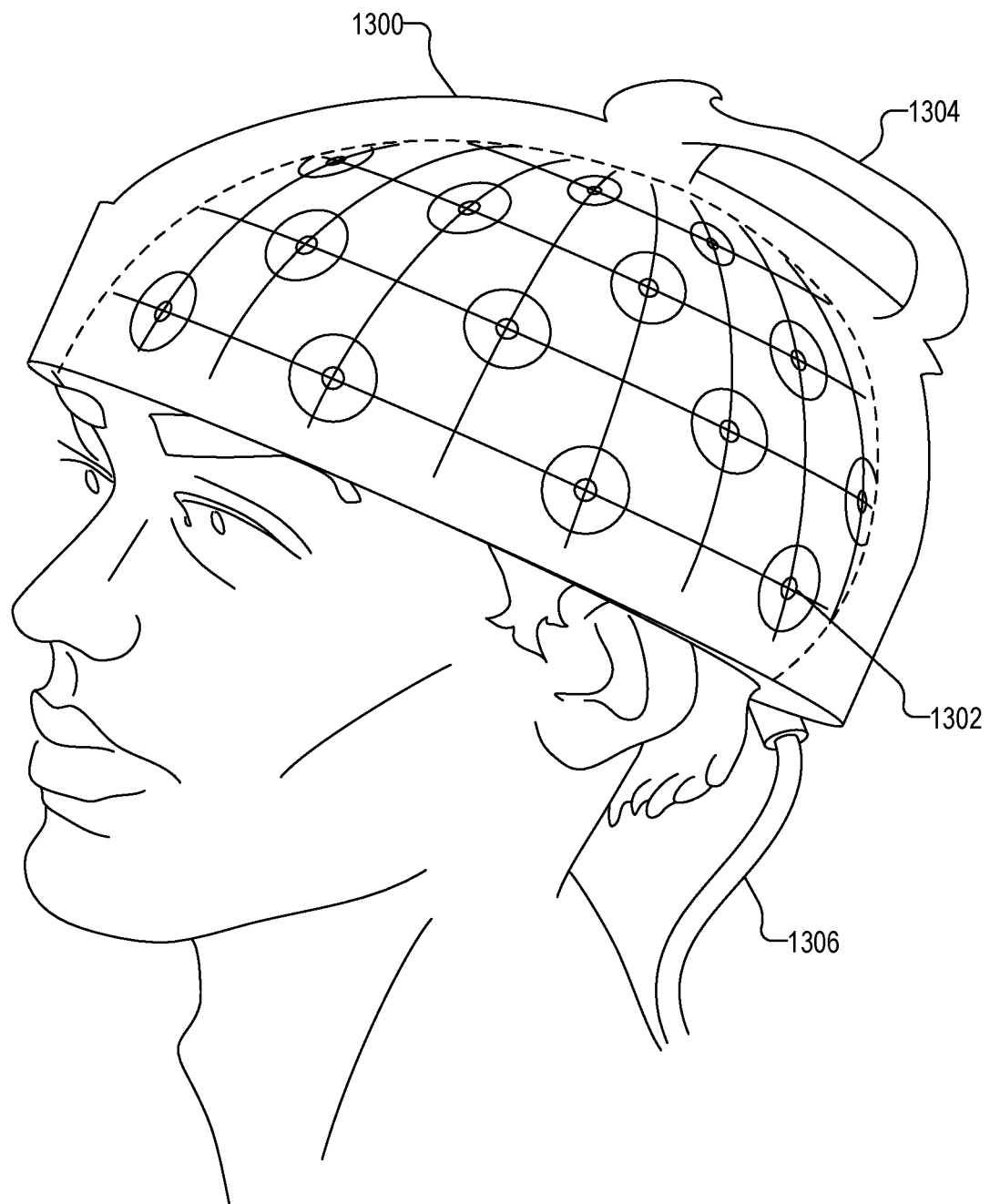
FIGS. 13-18 illustrate embodiments of a wearable device that includes elements of the optical detection systems described herein.
Figure 14:
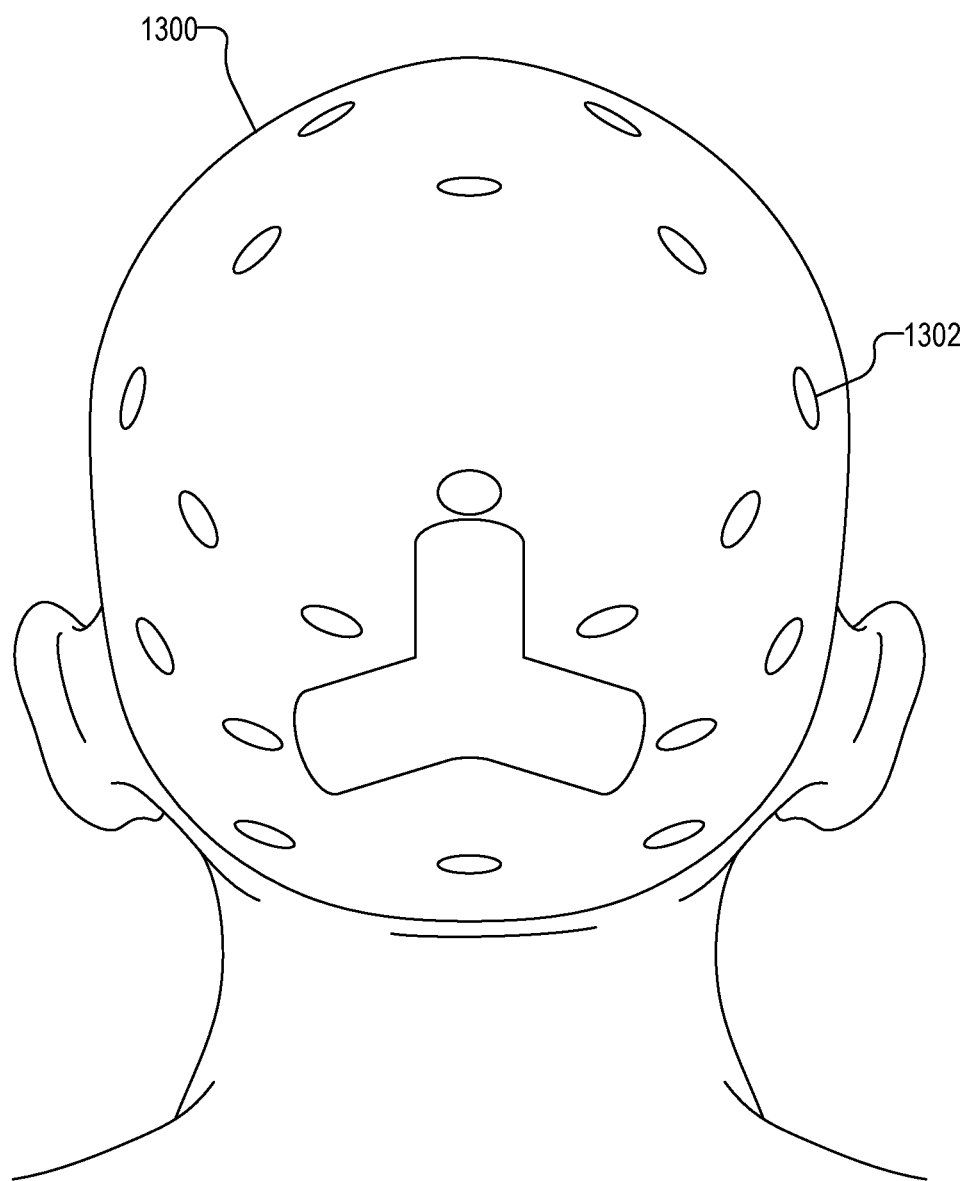
Figure 15:
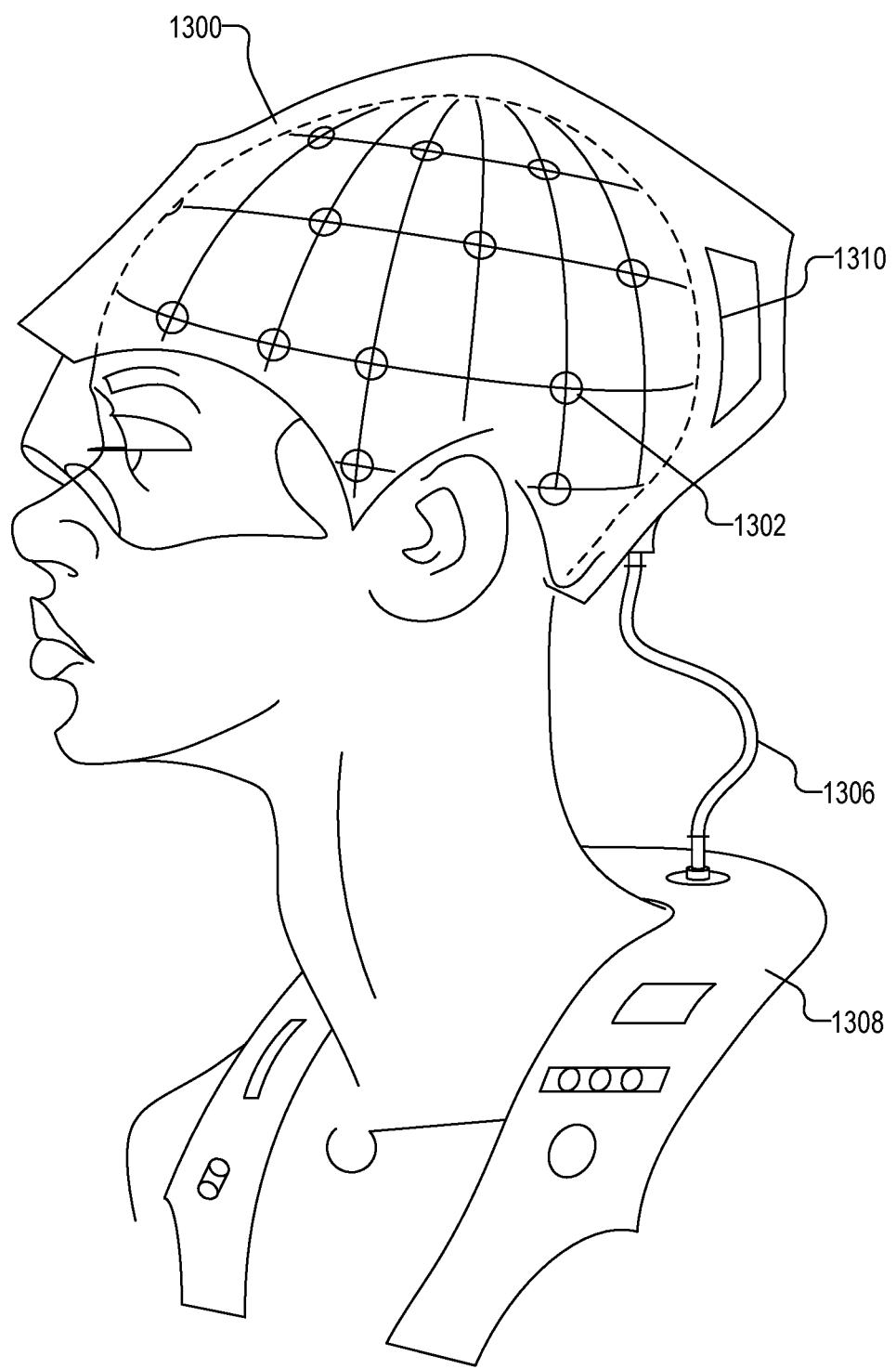

FIG. 13 illustrates an embodiment of a wearable device 1300 in the form of a helmet with a handle 1304. A cable 1306 extends from the wearable device 1300 for attachment to a battery or hub (with components such as a processor or the like). FIG. 14 illustrates another embodiment of a wearable device 1300 in the form of a helmet showing a back view. FIG. 15 illustrates a third embodiment of a wearable device 1300 in the form of a helmet with the cable 1306 leading to a wearable garment 1308 (such as a vest or partial vest) that can include a battery or a hub. Alternatively or additionally, the wearable device 1300 can include a crest 1310 or other protrusion for placement of the hub or battery.

Figure 16:
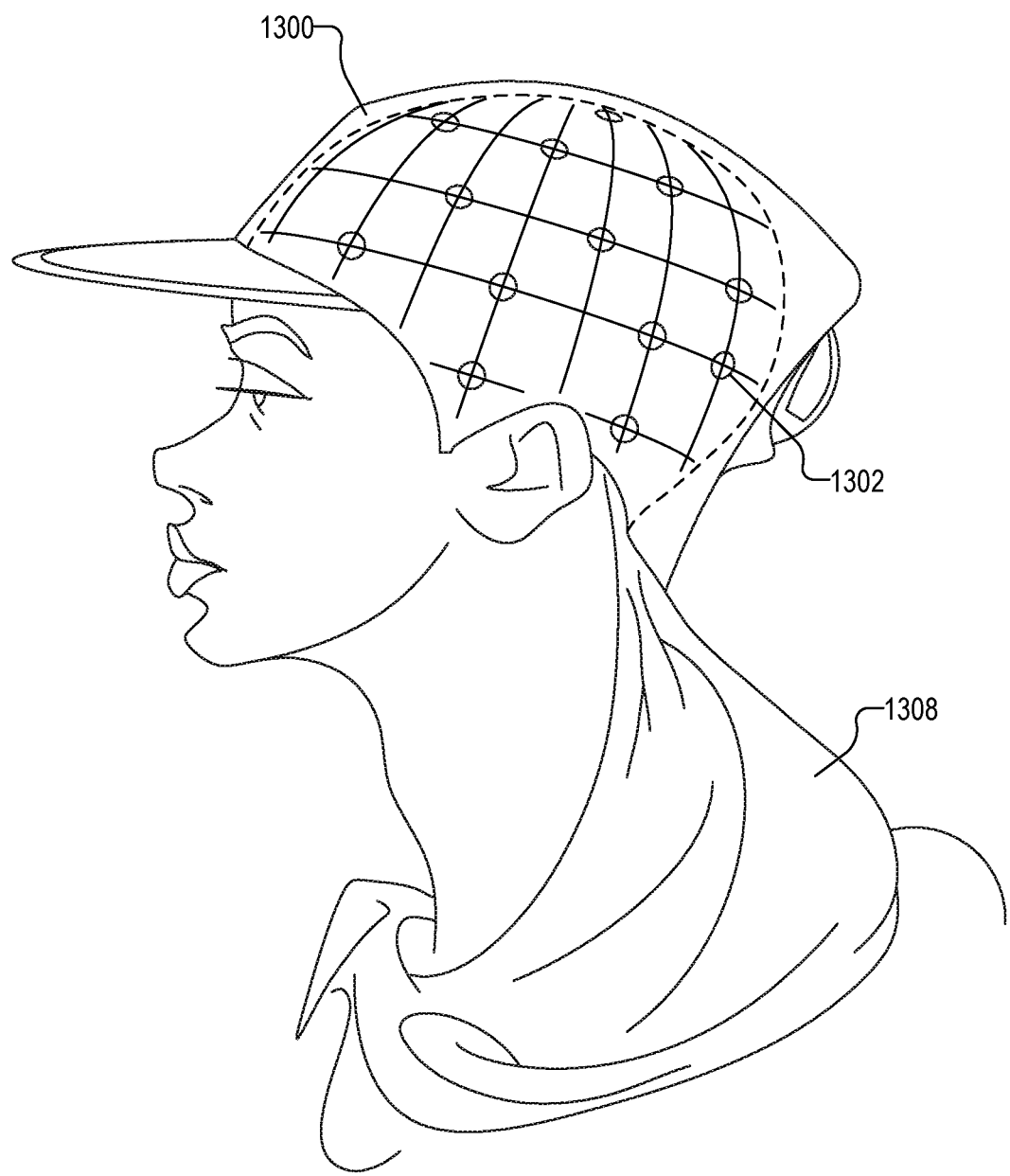
Figure 17:
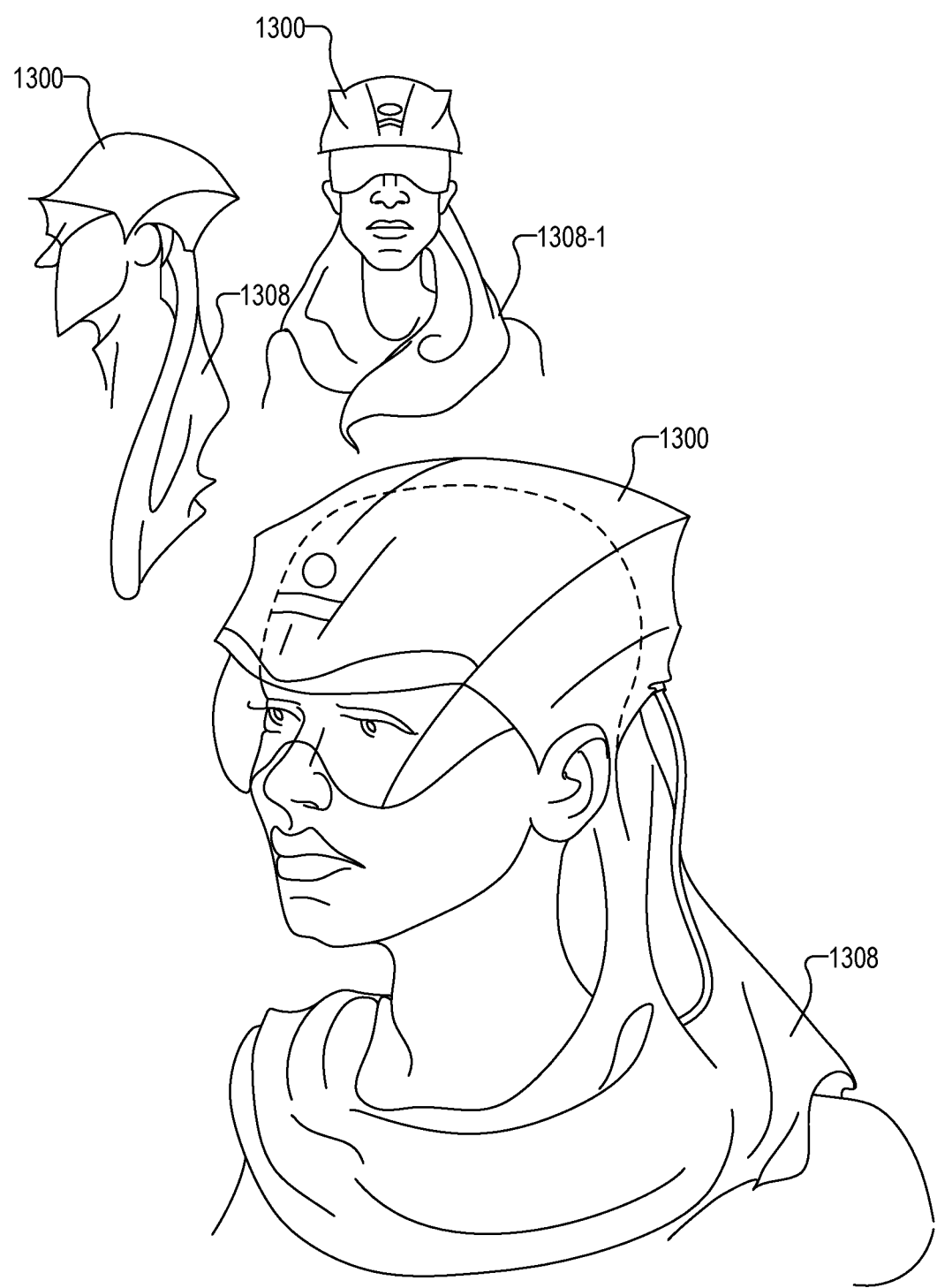
Figure 18:
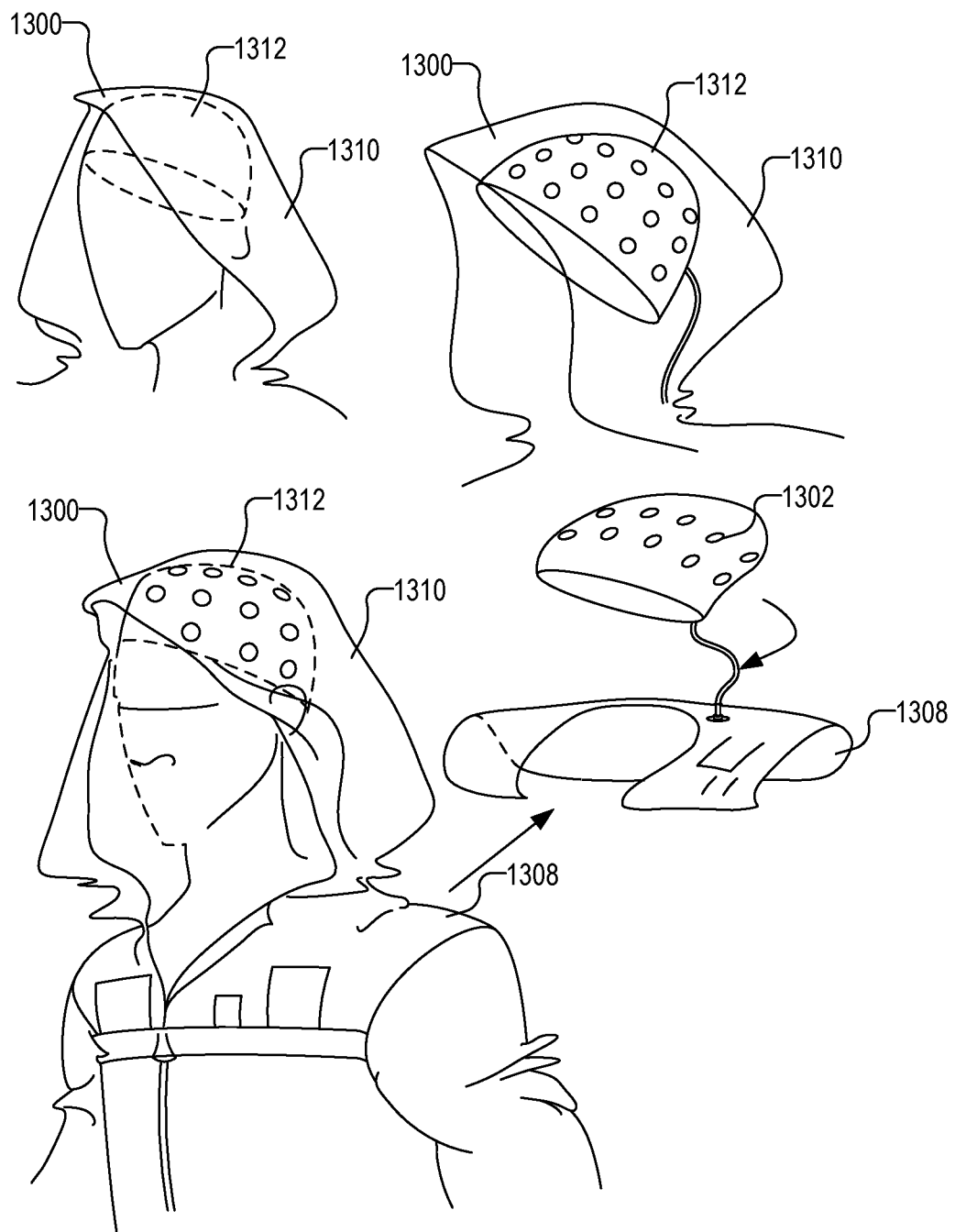

FIG. 16 illustrates another embodiment of a wearable device 1300 in the form of a cap with a wearable garment 1308 in the form of a scarf that may contain or conceal a cable, battery, and/or hub. FIG. 17 illustrates additional embodiments of a wearable device 1300 in the form of a helmet with a one-piece scarf 1308 or two-piece scarf 1308-1. FIG. 18 illustrates an embodiment of a wearable device 1300 that includes a hood 1310 and a beanie 1312 which contains the modules 1302, as well as a wearable garment 1308 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 19:
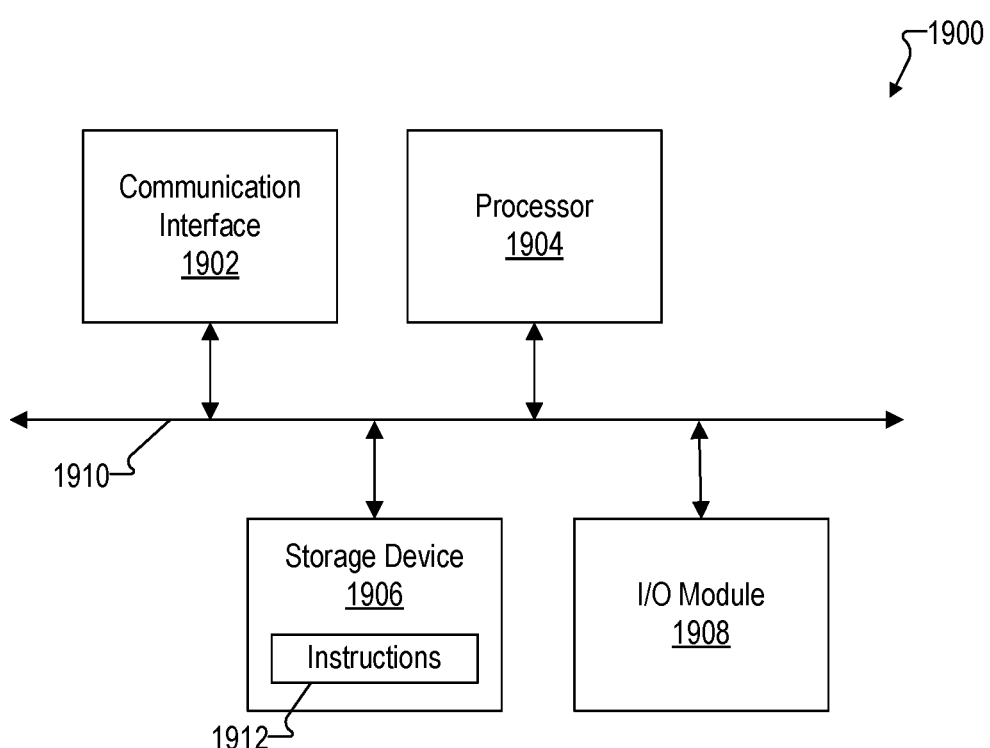
FIG. 19 illustrates an exemplary computing device.

FIG. 19 illustrates an exemplary computing device 1900 that may be specifically configured to perform one or more of the processes described herein. Any of the systems, units, computing devices, and/or other components described herein may be implemented by computing device 1900.

As shown in FIG. 19, computing device 1900 may include a communication interface 1902, a processor 1904, a storage device 1906, and an input/output ("I/O") module 1908 communicatively connected one to another via a communication infrastructure 1910. While an exemplary computing device 1900 is shown in FIG. 19, the components illustrated in FIG. 19 are not intended to be limiting. Additional or alternative components may be used in other embodiments. Components of computing device 1900 shown in FIG. 19 will now be described in additional detail.

Communication interface 1902 may be configured to communicate with one or more computing devices. Examples of communication interface 1902 include, without limitation, a wired network interface (such as a network interface card), a wireless network interface (such as a wireless network interface card), a modem, an audio/video connection, and any other suitable interface.

Processor 1904 generally represents any type or form of processing unit capable of processing data and/or interpreting, executing, and/or directing execution of one or more of the instructions, processes, and/or operations described herein. Processor 1904 may perform operations by executing computer-executable instructions 1912 (e.g., an application, software, code, and/or other executable data instance) stored in storage device 1906.

Storage device 1906 may include one or more data storage media, devices, or configurations and may employ any type, form, and combination of data storage media and/or device. For example, storage device 1906 may include, but is not limited to, any combination of the non-volatile media and/or volatile media described herein. Electronic data, including data described herein, may be temporarily and/or permanently stored in storage device 1906. For example, data representative of computer-executable instructions 1912 configured to direct processor 1904 to perform any of the operations described herein may be stored within storage device 1906. In some examples, data may be arranged in one or more databases residing within storage device 1906.

I/O module 1908 may include one or more I/O modules configured to receive user input and provide user output. I/O module 1908 may include any hardware, firmware, software, or combination thereof supportive of input and output capabilities. For example, I/O module 1908 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1908 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1908 is configured to provide graphical data to a display for presentation to a user. The graphical data may be representative of one or more graphical user interfaces and/or any other graphical content as may serve a particular implementation.

Figure 20:
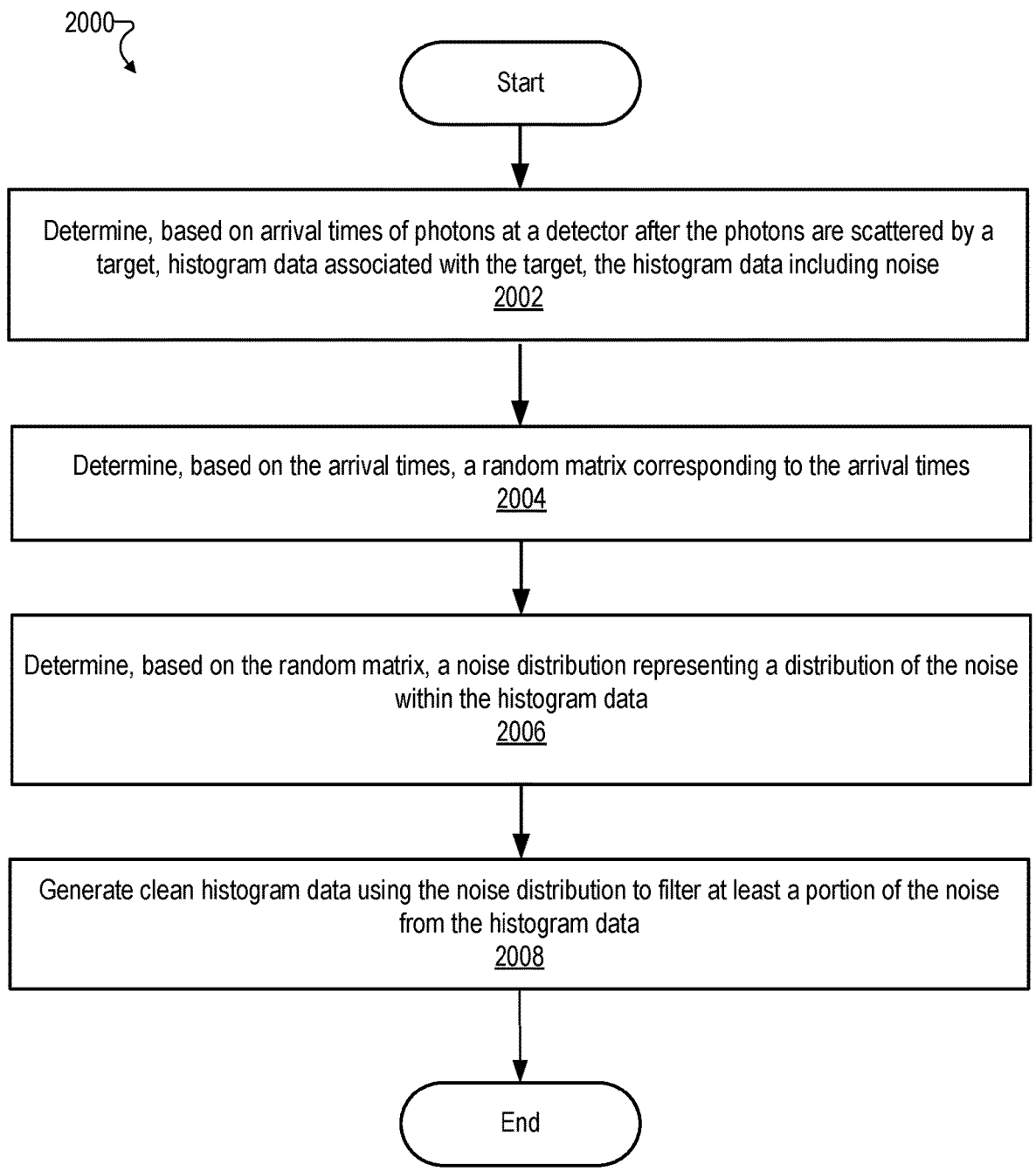
FIG. 20 illustrates an exemplary method.

FIG. 20 illustrates an exemplary method 2000 that may be performed by processing unit 1006 and/or any implementation thereof. While FIG. 20 illustrates exemplary operations according to one embodiment, other embodiments may omit, add to, reorder, and/or modify any of the operations shown in FIG. 20. Each of the operations shown in FIG. 20 may be performed in any of the ways described herein.

At operation 2002, a processing unit of an optical measurement system determines, based on arrival times of photons at a detector after the photons are scattered by a target, histogram data associated with the target, the histogram data including noise.

At operation 2004, the processing unit determines, based on the arrival times, a random matrix corresponding to the arrival times.

At operation 2006, the processing unit determines, based on the random matrix, a noise distribution representing a distribution of the noise within the histogram data.

At operation 2008, the processing unit generates clean histogram data using the noise distribution to filter at least a portion of the noise from the histogram data.

An illustrative optical measurement system includes a light source configured to emit light directed at a target within a user. The system further includes a detector configured to detect photon arrival times for photons of the light after the light is scattered by the target. The system further includes a processing unit configured to determine, based on the photon arrival times, histogram data associated with the target, the histogram data including noise. The processing unit is further configured to determine, based on the photon arrival times, a random matrix corresponding to the photon arrival times. The processing unit is further configured to determine, based on the random matrix, a noise distribution representing a distribution of the noise within the histogram data. The processing unit is further configured to generate clean histogram data using the noise distribution to filter at least a portion of the noise from the histogram data.

Another illustrative optical measurement system includes a head-mountable component configured to be attached to a head of the user, the head-mountable component comprising an array of photodetectors configured to detect photons from a light pulse after the light pulse reflects off at least one of a target within the head. The optical measurement system further includes processing unit configured to determine, based on photon arrival times of the photons at the photodetectors, histogram data associated with the target, the histogram data including noise. The processing unit is further configured to determine, based on the photon arrival times, a random matrix corresponding to the photon arrival times. The processing unit is further configured to determine, based on the random matrix, a noise distribution representing a distribution of the noise within the histogram data. The processing unit is further configured to generate clean histogram data using the noise distribution to filter at least a portion of the noise from the histogram data.

An illustrative method includes determining, by a processing unit and based on photon arrival times of photons at a detector after the photons are scattered by a target, histogram data associated with the target, the histogram data including noise. The method further includes determining, by the processing unit and based on the photon arrival times, a random matrix corresponding to the photon arrival times. The method further includes determining, by the processing unit and based on the random matrix, a noise distribution representing a distribution of the noise within the histogram data. The method further includes generating, by the processing unit, clean histogram data using the noise distribution to filter at least a portion of the noise from the histogram data.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
    a light source configured to emit light directed at a target, the target comprising a portion of a brain of a user;
    a detector configured to detect photon arrival times for photons of the light after the light is scattered by the target; and
    a processing unit configured to:
        determine, based on the photon arrival times, histogram data associated with the target, the histogram data including noise;
        generate, based on the histogram data, a histogram data matrix;
        determine, based on the histogram data matrix, a random matrix corresponding to the photon arrival times;
        determine, based on the random matrix and using random matrix theory, a noise distribution representing a distribution of the noise within the histogram data;
        generate clean histogram data using the noise distribution to filter at least a portion of the noise from the histogram data; and
        detect, based on the clean histogram data, neural activity of the user.

2. The optical measurement system of claim 1, wherein:
    the light comprises a plurality of light pulses; and
    the histogram data comprises a plurality of time bins that each correspond to a different period of time relative to the light pulses.

3. The optical measurement system of claim 2, wherein:
    the histogram data matrix is based on a number of the plurality of light pulses and a number of the plurality of time bins; and
    the random matrix comprises a correlation matrix based on the histogram data matrix.

4. The optical measurement system of claim 3, wherein the determining the noise distribution comprises determining a Marchenko-Pastur distribution of eigenvalues based on the random matrix.

5. The optical measurement system of claim 4, wherein the using the noise distribution to filter at least the portion of the noise comprises:
    determining signal eigenvalues outside boundaries of the Marchenko-Pastur distribution and signal eigenvectors corresponding to the signal eigenvalues; and
    determining a clean histogram data matrix based on the signal eigenvectors.

6. The optical measurement system of claim 5, wherein the generating the clean histogram data comprises determining histogram data based on the clean histogram data matrix.

7. The optical measurement system of claim 1, further comprising an additional detector configured to detect additional photon arrival times for photons of the light after the light is scattered by the target; and
    wherein the determining the histogram data is further based on the additional photon arrival times.

8. A wearable system for use by a user comprising:
    a head-mountable component configured to be attached to a head of the user, the head-mountable component comprising an array of photodetectors configured to detect photons of light after the light reflects off a target within the head; and a processing unit configured to:
  determine, based on photon arrival times of the photons at the photodetectors, histogram data associated with the target, the histogram data including noise;
  generate, based on the histogram data, a histogram data matrix;
  determine, based on the histogram data matrix, a random matrix corresponding to the photon arrival times;
  determine, based on the random matrix and using random matrix theory, a noise distribution representing a distribution of the noise within the histogram data;
  generate clean histogram data using the noise distribution to filter at least a portion of the noise from the histogram data; and
  detect, based on the clean histogram data, neural activity of the user.

9. The wearable system of claim 8, wherein:
the light comprises a plurality of light pulses; and
the histogram data comprises a plurality of time bins that each correspond to a different period of time relative to the light pulses.

10. The wearable system of claim 9, wherein:
the histogram data is matrix based on a number of the plurality of light pulses and a number of the plurality of time bins; and
the random matrix comprises a correlation matrix based on the histogram data matrix.

11. The wearable system of claim 10, wherein the determining the noise distribution comprises determining a Marchenko-Pastur distribution of eigenvalues based on the random matrix.

12. The wearable system of claim 11, wherein the using the noise distribution to filter at least the portion of the noise comprises:
  determining signal eigenvalues outside boundaries of the Marchenko-Pastur distribution and signal eigenvectors corresponding to the signal eigenvalues; and
  determining a clean histogram data matrix based on the signal eigenvectors.

13. The wearable system of claim 12, wherein the generating the clean histogram data comprises determining histogram data based on the clean histogram data matrix.

14. A system comprising:
a memory storing instructions;
a processor communicatively coupled to the memory and configured to execute the instructions to:
  determine, based on photon arrival times of photons at a detector after the photons are scattered by a target, histogram data associated with the target, the target comprising a portion of a brain of a user, the histogram data including noise;
  generate, based on the histogram data, a histogram data matrix;
  determine, based on the histogram data matrix, a random matrix corresponding to the photon arrival times;
  determine, based on the random matrix and using random matrix theory, a noise distribution representing a distribution of the noise within the histogram data;
  generate clean histogram data using the noise distribution to filter at least a portion of the noise from the histogram data; and
  detect, based on the clean histogram data, neural activity of the user.

15. The system of claim 14, wherein:
the photons are from a plurality of light pulses; and
the histogram data comprises a plurality of time bins that each correspond to a different period of time relative to the light pulses.

16. The system of claim 15, wherein:
the histogram data matrix is based on a number of the plurality of light pulses and a number of the plurality of time bins; and
the random matrix comprises a correlation matrix based on the histogram data matrix.

17. The system of claim 16, wherein the determining the noise distribution comprises determining a Marchenko-Pastur distribution of eigenvalues based on the random matrix.

18. The system of claim 17, wherein the using the noise distribution to filter at least the portion of the noise comprises:
  determining signal eigenvalues outside boundaries of the Marchenko-Pastur distribution and signal eigenvectors corresponding to the signal eigenvalues; and
  determining a clean histogram data matrix based on the signal eigenvectors.

19. The system of claim 18, wherein the generating the clean histogram data comprises determining histogram data based on the clean histogram data matrix.

20. A method comprising:
  determining, by a processing unit and based on photon arrival times of photons at a detector after the photons are scattered by a target, histogram data associated with the target, the target comprising a portion of a brain of a user, the histogram data including noise;
  generating, based on the histogram data, a histogram data matrix;
  determining, based on the histogram data matrix, a random matrix corresponding to the photon arrival times;
  determining, based on the random matrix and using random matrix theory, a noise distribution representing a distribution of the noise within the histogram data; and
  determining, by the processing unit and based on the photon arrival times, a random matrix corresponding to the photon arrival times;
  determining, by the processing unit and based on the random matrix, a noise distribution representing a distribution of the noise within the histogram data;
  generating, by the processing unit, clean histogram data using the noise distribution to filter at least a portion of the noise from the histogram data; and
  detecting, based on the clean histogram data, neural activity of the user.

21. The method of claim 20, wherein:
the photons are from a plurality of light pulses; and
the histogram data comprises a plurality of time bins that each correspond to a different period of time relative to the light pulses.

22. The method of claim 21, wherein the
histogram data matrix is based on a number of the plurality of light pulses and a number of the plurality of time bins, and
wherein the random matrix comprises a correlation matrix based on the histogram data matrix.

23. The method of claim 22, wherein the determining the noise distribution comprises determining a Marchenko-Pastur distribution of eigenvalues based on the random matrix.

24. The method of claim 23, wherein the using the noise distribution to filter at least the portion of the noise comprises:

determining signal eigenvalues outside boundaries of the Marchenko-Pastur distribution and signal eigenvectors corresponding to the signal eigenvalues; and determining a clean histogram data matrix based on the signal eigenvectors.

25. The method of claim 24, wherein the generating the clean histogram data comprises determining histogram data based on the clean histogram data matrix.

* * * * *